(12) United States Patent
Ewert et al.

(10) Patent No.: US 8,323,647 B2
(45) Date of Patent: Dec. 4, 2012

(54) HUMANIZED ANTIBODIES AGAINST THE β-AMYLOID PEPTIDE

(75) Inventors: Stefan Ewert, Allschwill (CH); Adrian Auf Der Maur, Dietikon (CH); Susann Cattepoel, Zurich (CH); Roger Nitsch, Zumikon (CH)

(73) Assignees: Delenex Therapeutics AG, Schlieren (CH); University of Zurich, Zurich (CH)

( * ) Notice: Subject to any disclaimer, the term of this patent is extended or adjusted under 35 U.S.C. 154(b) by 0 days.

(21) Appl. No.: 12/677,732

(22) PCT Filed: Sep. 15, 2008

(86) PCT No.: PCT/CH2008/000382
§ 371 (c)(1),
(2), (4) Date: Jun. 9, 2010

(87) PCT Pub. No.: WO2009/033309
PCT Pub. Date: Mar. 19, 2009

(65) Prior Publication Data
US 2011/0020220 A1 Jan. 27, 2011

Related U.S. Application Data

(60) Provisional application No. 61/083,698, filed on Jul. 25, 2008, provisional application No. 60/993,612, filed on Sep. 13, 2007.

(51) Int. Cl.
*A61K 39/395* (2006.01)
*C07K 16/18* (2006.01)
*C12P 21/08* (2006.01)

(52) U.S. Cl. ............ 424/133.1; 424/135.1; 424/139.1; 530/387.3; 530/387.9; 530/391.3; 530/391.7

(58) Field of Classification Search .................. None
See application file for complete search history.

(56) References Cited

U.S. PATENT DOCUMENTS

2003/0073655 A1 4/2003 Chain
2009/0311251 A1* 12/2009 Auf Der Maur et al. .. 424/133.1

FOREIGN PATENT DOCUMENTS

| WO | WO 97/26010 | 7/1997 |
| WO | WO 2004/032868 | 4/2004 |
| WO | WO 2004056312 * | 7/2004 |
| WO | WO 2006/036291 | 4/2006 |
| WO | WO 2006/118959 | 11/2006 |
| WO | WO 2007/022015 A1 | 2/2007 |
| WO | WO 2008/122441 A2 | 10/2008 |
| WO | WO 20091033743 A1 | 3/2009 |

OTHER PUBLICATIONS

Casset et al. Biochem Biophys Res Comm. 2003; 307:198-205.*
Chen et al. J Mol Biol. 1999; 293:865-881.*
Holm et al. Mol Immunol. 2007; 44(6):1075-1084.*
MacCallum et al. J Mol Biol. 1996; 262:732-745.*
Padlan et al. (Proc Natl Acad Sci USA, 1989; 86:5938-5942.*
Paul, Fundamental Immunology, 1993, pp. 292-295.*
Rudikoff et al. Proc Natl Acad Sci USA, 1982; 79(6):1979-1983.*
Vajdos et al. J Mol Biol. 2002; 320(2):415-428.*
Vickers JC, Drugs Aging. 2002; 19(7):487-494.*
Walker et al. J Neuropathol. Exp. Neurol. 1994; 53(4):377-383.*
International Search Report in corresponding PCT/CH2008/000382 dated Nov. 20, 2008.
Written Opinion in corresponding PCT/CH2008/000382.
International Preliminary Examination Report in corresponding PCT/CH2008/000382.
Zameer et al., "Single Chain Fv Antibodies against the 25-35-Aβ Fragment Inhibit Aggregation and Toxicity of Aβ42," *Biochemistry* 2006, 45, 11532-11539.
Liu et al., "Single Chain Variable Fragments against β-Amyloid (Aβ) Can Inhibit Aβ Aggregation and Prevent Aβ-Induced Neurotoxicity," *Biochemistry* 2004, 43, 6959-6967.
Mohajeri et al., "Assessment of the Bioactivity of Antibodies against β-Amyloid Peptide in vitro and in vivo," *Neurodegenerative Dis* 2004, 1, 160-167.
Mohajeri et al., Passive Immunization against β-Amyloid Peptide Protects Central Nervous System (CNS) Neurons from Increased Vulnerability Associated with an Alzheimer's Disease-causing Mutation, *The Journal of Biological Chemistry*, 277, 36, 33012-33017, 2002.
Lichtlen et al., "Antibody-based approaches in Alzheimer's research; safety, pharmacokinetics, metabolism, and analytical tools," *Journal of Neurochemistry* 104,4, 859-874, Feb. 2008.
Smith, S.V., "Molecular imaging with copper -64," *Journal of Inorganic Chemistry*, 98, 1874-1901, 2004.
Vasilevko, et al., "Novel approaches for immunotherapeutic intervention in Alzheimer's disease," *Neurochemistry International* 49, 113-126, 2006.
Alfthan et al., "Properties of a single-chain antibody containing different linker peptides," *Protein Eng.* 8:725-731 (1995).
Altschul et al., "Gapped Blast and PSI-Blast: a new generation of protein database search programs," *Nucleic Acids Res.* 25(17):3389-3402 (1997).
Altschul et al., "Basic Local Alignment Search Tool." *J. Mol. Biol.* 215:403-410 (1990).
Atha, et al., "Mechanism of Precipitation of Proteins by Polyethylene Glycols," *Journal of Biological Chemistry* 256(23):12108-12117 (1981).
Bacskai et al., "Imaging of amyloid-β deposits in brains of living mice permits direct observation of clearance of plaques with immunotherapy," *Nat. Med.* 7(3):369-372 (2001).

(Continued)

*Primary Examiner* — Elizabeth C Kemmerer
*Assistant Examiner* — Kimberly A Ballard
(74) *Attorney, Agent, or Firm* — Lathrop & Gage LLP; James H. Velema, Esq.

(57) ABSTRACT

The invention discloses an isolated antibody that selectively binds to the C-terminal part of Abeta and is humanized or fully human. The antibody of the invention is capable of preventing oligomerization of Abeta. Furthermore, a method of diagnosis comprising the steps of: (i) Labelling an antibody; (ii) Administering an effective dose of said antibody intranasally or systemically to a subject; and (iii) Detecting the concentration and/or presence of the labelled antibody in body parts of the subject is disclosed.

39 Claims, 17 Drawing Sheets

OTHER PUBLICATIONS

Bacskai et al., Non-Fc-Mediated Mechanisms are Involved in Clearance of Amyloid-β In Vivo by Immunotherapy. *J. Neurosci.* 22(18):7873-7878 ,(2002):.

Bard et al., "Peripherally administered antibodies against amyloid β peptide enter the central nervous system and reduce pathology in a mouse model of Alzheimer disease," *Nat. Med.* 6(8): 916-919 (2000).

Brookmeyer R et al., "Forecasting the global burden of Alzheimer's disease," *Journal of Alzheimer's and Dementia* 3:186-191 (2007).

Burmester et al., "Construction of scFv fragments from hybridoma or spleen cells by PCR assembly," in: *Antibody Engineering*, R. Kontermann and S. Dübel, Eds., Springer-Verlag, Berlin Heidelberg, pp. 19-40 (2001).

Chothia et al., "Canonical Structures for the Hypervariable Regions of Immunoglobulins," *J Mol Biol* 196: 901-917 (1987).

Davies et al., "Antibody-Antigen Complexes," *Ann. Rev. Biochem.* 59:439-473 (1990).

DeMattos et al., "Peripheral anti-Aβ antibody alters CNS and plasma Aβ clearance and decreases brain Aβ burden in a mouse model of Alzheimer's disease," *Proc. Natl. Acad. Sci. USA* 98: 8850-8855 (2001).

Frenkel et al., "Immunization against Alzheimer's β-amyloid plaques via EFRH phage administration," *Proc. Natl. Acad. Sci. USA* 971: 1455-11459 (2000).

Gaugler et al.,, "Modulation of Alzheimer's pathology by cerebroventricular grafting of hybridoma cells expressing antibodies against Aβ in vivo," *FEBS Letters* 579:753-756 (2005).

Güntert et al., "High sensitivity analysis of amyloid-beta peptide composition in amyloid deposits from human and PS2APP mouse brain," *Neuroscience* 143: 461-475 (2006).

Holliger et al., "Engineered antibody fragments and the rise of single domains," *Nat. Biotechnol.* 23(9): 1126-1136 (2005).

Kabat et al. *Sequences of proteins of immunological interest.*, National Institutes of Health, 5th Ed. Bethesda, MD. Available online at books.google.com/books?id=3jMvZYW2ZtwC& printsec=frontcover&source=gbs_v2_summary_r& cad=0#v=onepage&q&f=false].

Klein, W.L., "Aβ toxicity in Alzheimer's disease: globular oligomers (ADDLs) as new vaccine and drug targets," *Neurochemistry International* 41: 345-352 (2002).

Knobloch et al., Intracellular Aβ and cognitive deficits precede β-amyloid deposition in transgenic arc Aβ mice. *Neurobiology of Aging*:1297-1306 (2007).

LeVine III, H., "Thioflavine T interaction with synthetic Alzheimer's disease beta-amyloid peptides: Detection of amyloid aggregation in solution," *Protein Science* 2: 404-410 (1993).

Miller et al., "Monoclonal Antibody Therapeutic Trials in Seven Patients With T-cell Lymphoma," *Blood* 62(5):988-995 (1983).

Schroff et al., "Human Anti-Murine Immunoglobulin Responses in Patients Receiving Monoclonal Antibody Therapy," *Cancer Research* 45:879-885 (1985).

Wörn et al., "Correlation Between In Vitro Stability and In Vivo Performance of Anti-GCN4 Intrabodies as Cytoplasmic Inhibitors," *Journal of Biological Chemistry* 275(4):2795-803 (2000).

Bard et al., "Epitope and isotype specificities of antibodies to beta-amyloid peptide for protection against Alheimer's disease-like neuropathology,"Proceedings of the National Academy of Sciences of the United States of America, National Academy of Science, Washington, DC., United States, vol. 100, No 4. Feb. 18, 2003, pp. 2023-2028.

Gaskin et al., "Human Antibodies Reactive With Beta-Amyloid Protein in Alzheimer'S Disease," Journal of Experimental Medicine, Rockefeller University Press, JP, vol. 177, No. 4, Apr. 1, 1993, pp. 1181-1186.

Horikoshi et al., "Development of Abeta terminal end-specific antibodies and sensitive ELISA for Abeta variant," Biochemical and Biophysical Research Communications, Academic Press Inc., Orlando, Florida, United States, vol. 319, No. 3, Jul. 2, 2004, pp. 733-737.

Iwatsubo et al., Visualization of Abeta42(43) and Abeta40 in senile plaques with end-specific Abeta monoclonals: evidence that an initially deposited species is Abeta42(43). Neuron, 1994: 13: 45-53.

Berezovska et al., "Notch1 and Amyloid Precursor Protein Are Competitive Substrates for Presenilin1-dependent—Secretase Cleavage*", The Journal of Biological Chemistry, vol. 276, No. 32, Issue of Aug. 10, 2001, pp. 30018-30023

Cattepoel et al., (2011) Chronic Intranasal Treatment with an Anti-Ab30-42 scFv Antibody Ameliorates Amyloid Pathology in a Transgenic Mouse Model of Alzheimer's Disease. PLoS One 6(4): e18296. doi:10.1371/journal.pone.0018296.

Habicht et al., "Directed selection of a conformational antibody domain that prevents mature amyloid fibril formation by stabilizing A protofibrils", PNAS, vol. 104, No. 49, Dec. 4, 2007, pp. 19232-19237.

* cited by examiner

Fig. 1

```
ESBA212   ADIVLTQSPSSLSASVGDRVTLTCRASSSV-NYMHWYQQRPGKPPKALIYATSNLASGVP  59
Framework AEIVLTQSPSSLSASVGDRVTLTCRASQGIRNELAWYQQRPGKAPKRLIYAGSILQSGVP  60
          *:************************.: .: ** .***********.** ***** * ****

ESBA212   SRFSGSGSGTEFTLTISSLQPEDVAVYYCQQWRTNPPTFGQGTKLEVKR  108
Framework S-FSGSGSGTEFTLTISSLQPEDVAVYYCQQYYSLPYMFGQGTKVDIKR  108
          * *****************************; * *******:: :**

22C4      -DIVLTQSPAILSASPGEKVTLTCRASSSVNYMHWYQQKPGSPPKAWIYATSNLASGVP  59
ESBA212   ADIVLTQSPSSLSASVGDRVTLTCRASQGIRNELAWYQQRPGKPPKPPKALIYATSNLASGVPS  60
          *********:****.*:***********  : *** **:**.***** *********.

22C4      RFSASGSGTSYSLTISRVEAEDAATYYCQQWRTNPPTFGAGTKLELKR  107
ESBA212   RFSGSGSGTEFTLTISSLQPEDVAVYYCQQWRTNPPTFGQGTKLEVKR  108
          ***:.****:::****  :: ****************.*****:**

22C4      -DIVLTQSPAILSASPGEKVTLTCRASSSVNYMHWYQQKPGSPPKAWIYATSNLASGVP  58
ESBA212   ADIVLTQSPSSLSASVGDRVTLTCRASQGIRNELAWYQQRPGKPPKPPKALIYATSNLASGVP  59
Framework AEIVLTQSPSSLSASVGDRVTLTCRASQGIRNELAWYQQRPGKAPKRLIYAGSILQSGVP  60
          :*******: **:*** .::******: *: ::.** **:*.:** **.*: .***

22C4      DRFSASGSGTSYSLTISRVEAEDAATYYCQQWRTNPPTFGAGTKLELKR  107
ESBA212   SRFSGSGSGTEFTLTISSLQPEDVAVYYCQQWRTNPPTFGQGTKLEVKR  108
Framework S-FSGSGSGTEFTLTISSLQPEDVAVYYCQQYYSLPYMFGQGTKVDIKR  108
          . ***.****: :*** .:. ** *****    : :* ***:::**
```

Fig. 2

```
ESBA212    QVQLVQSGPEVKKPGASVKVSCTASGYTFTEYTMHWVRQAPGQGLEWMGGVNPYNDNTSY- 60
Framework  QVQLVQSGAEVKKPGASVKVSCTASGYTFTGYFLHWVRQAPGQGLEWMGGVNPYNDNTSY-Y 59
           ******** ********************. ** . *********************** :*

ESBA212    IRKLQGRVTLTVDRSSSTAYMELTSLTSDDTAVYYCARYGG---LRPYYFPMDFWGQGTL 117
Framework  AQKFQDRVTLTRDTSIGTVYMELTSLTSDDTAVYYCARVPRGTYLDPWDY-FDYWGQGTL 118
            :*:.****** * .  .* .********************  *  : .:  : .:********

ESBA212    VTVSS 122
Framework  VTVSS 123
           *****
```

Fig. 3

```
22C4     QVQLQQSGPELVKPGASVKISCKTSGYTFTEYTMHWVKQSHGKSLEWIGGVNPYNDNTSY  60
ESBA212  QVQLVQSGPEVKKPGASVKVSCTASGYTFTEYTMHWVRQAPGQGLEWMGGVNPYNDNTSY  60
         **** ******: *:******:**. *********:**.:*:*:****:**********

22C4     IRKLQGKVTLTVDRSSSTAYMELRSLTSEDSAVYFCARYGGLRPYYFPMDEWGQGTSVTV 120
ESBA212  IRKLQGRVTLTVDRSSSTAYMELTSLTSDDTAVYYCARYGGLRPYYFPMDFWGQGTLVTV 120
         ******:****************.****:*:***:***************:*****:***

22C4     SS 122
ESBA212  SS 122
         **
```

Fig. 4

```
22C4         QVQLQQSGPELVKPGASVKISCKTSGYTFTEYTMHWVKQSHGKSLEWIGGVNPYNDNTSY 60
ESBA212      QVQLVQSGPEVKKPGASVKVSCTASGYTFTEYTMHWVRQAPGQGLEWMGGVNPYNDNTSY 60
Framework    QVQLVQSGAEVKKPGASVKVSCTASGYSFTGYFLHWVRQAPGQGLEWMMGRINPDSGDT-Y 59
             ****  *** *.*.:******:****:***.* ******* ****:**:  :.  : *

22C4         IRKLQGKVTLTVDRSSSTAYMELRSLTSEDSAVYFCARYGG---LRPYYFPMDFWGQGTS 117
ESBA212      IRKLQGRVTLTVDRSSSTAYMELTSLTSDDTAVYYCARYGG---LRPYYFPMDFWGQGTL 117
Framework    AQKFQDRVTLTRDTSIGTVYMELTSLTSDDTAVYYCARVPRGTYLDPWDY-FDYWGQGTL 118
              :*:  *:***** *:*  * .*.* ****..*  **:*** :  :: *. *******

22C4         VTVSS 122
ESBA212      VTVSS 122
Framework    VTVSS 123
             *****
```

Fig. 5
Fig. 5A 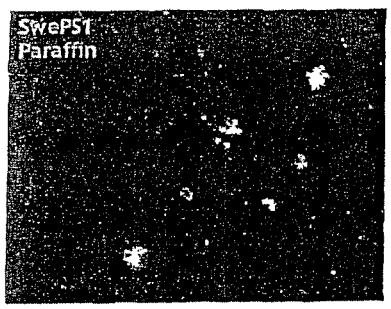 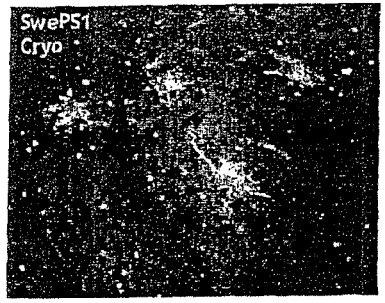 Fig. 5B
Fig. 5C 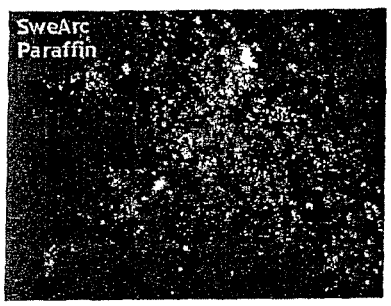 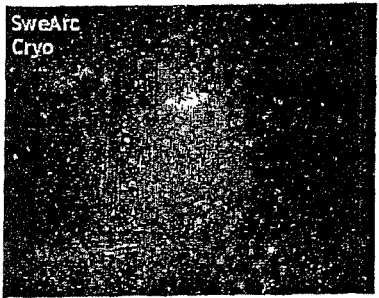 Fig. 5D
Fig. 6
Fig. 6A 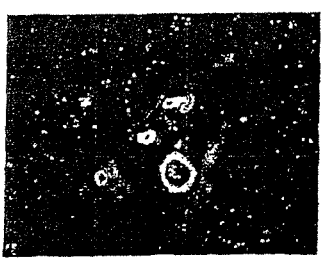 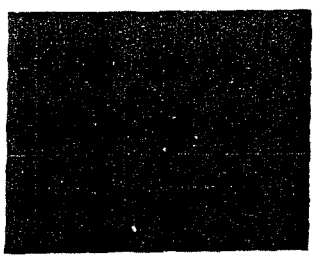 Fig. 6B
Fig. 6C  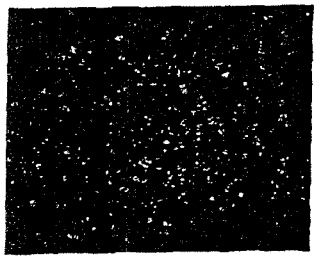 Fig. 6D Fig. 7
Fig. 7A
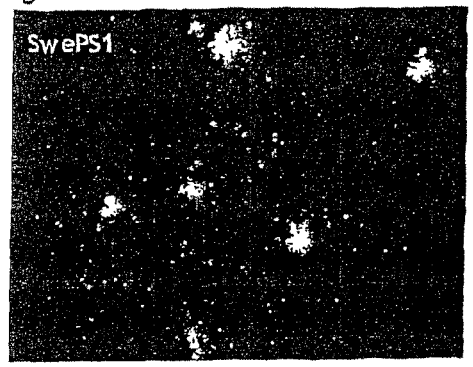
Fig. 7B
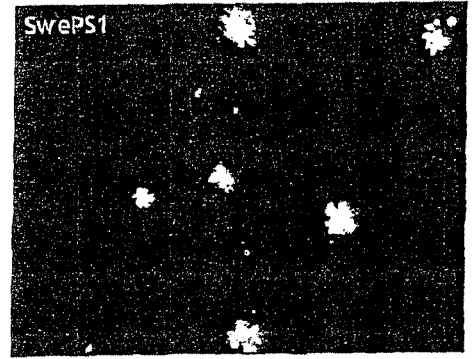
Fig. 8
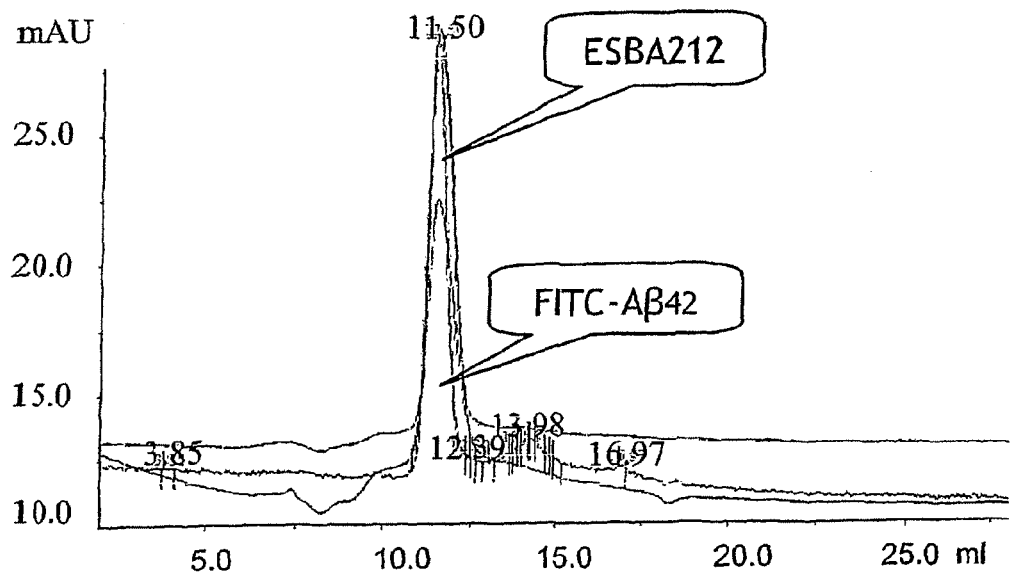
ESBA212Abeta42 005:10_UV3_495nm@ 03.PEAK
Fig. 8A

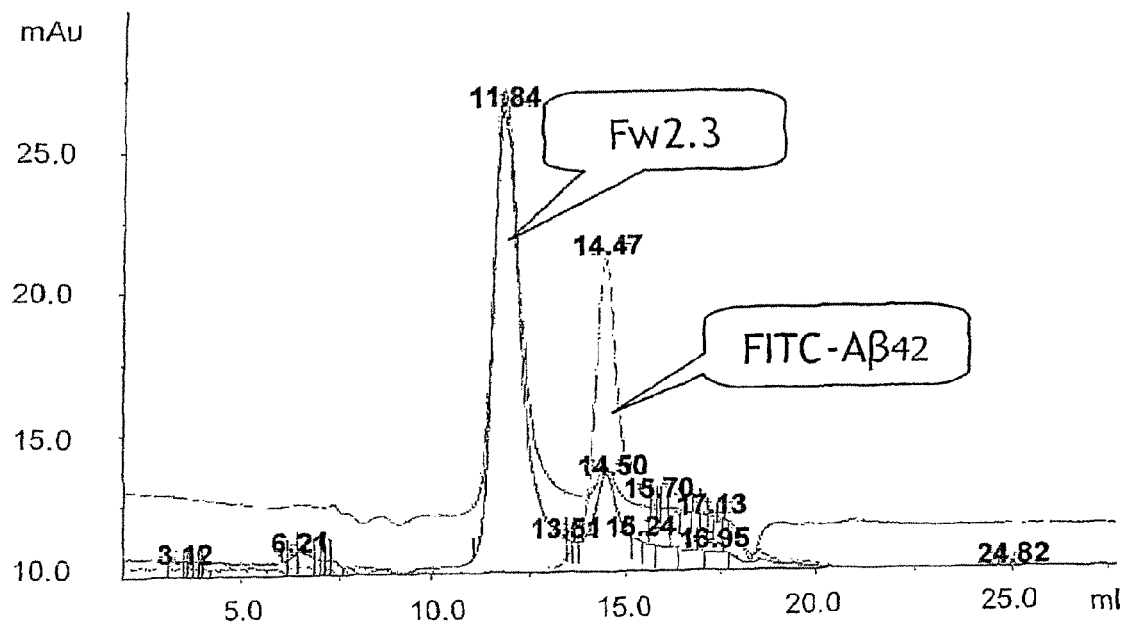
FW23Abeta42 006:10_UV2_280nm@02, PEAK
Fig. 8B
Fig. 9
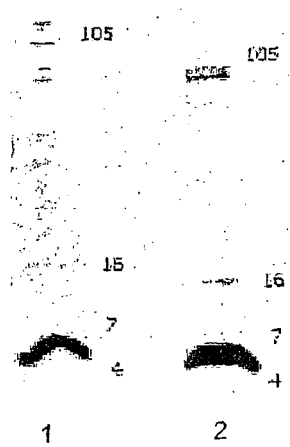
Fig. 9A
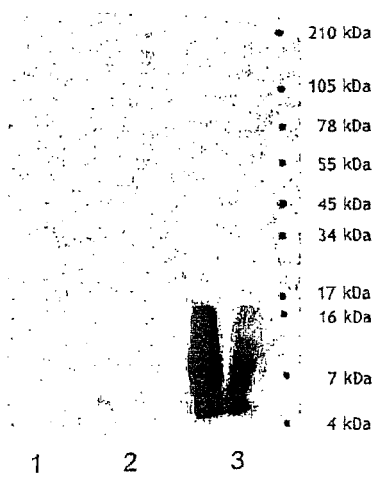
Fig. 9B

Fig. 15
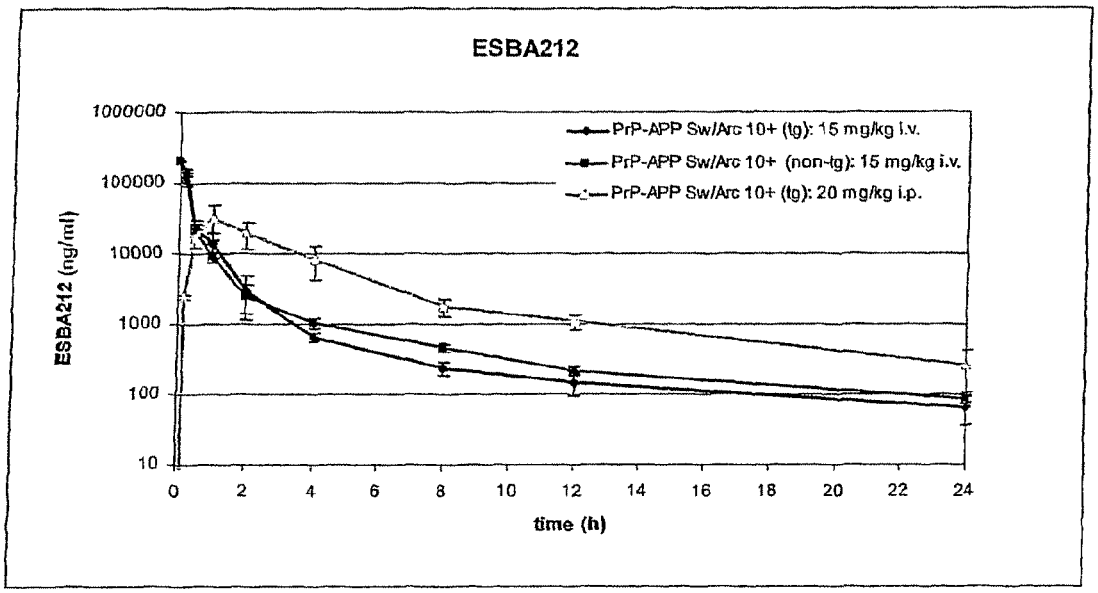
Fig. 16
Fig. 16 A        Fig. 16 B
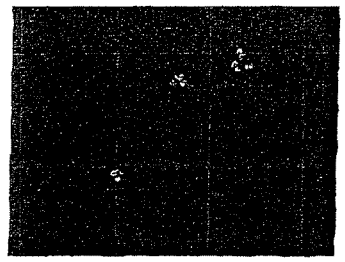   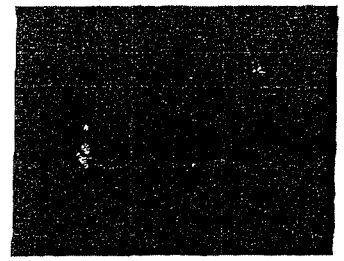

Fig. 17
Fig. 17 A
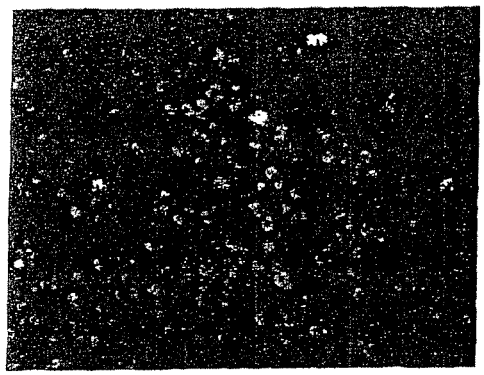
Fig. 17B
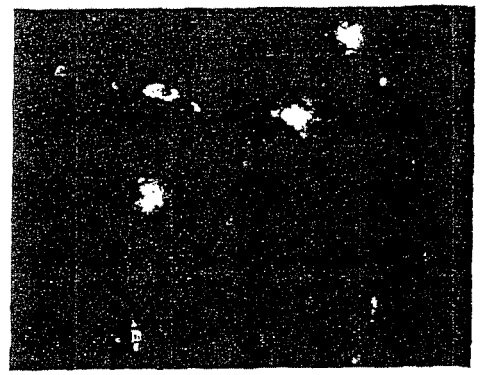
Fig. 18
Fig. 18A
Fig. 18 B
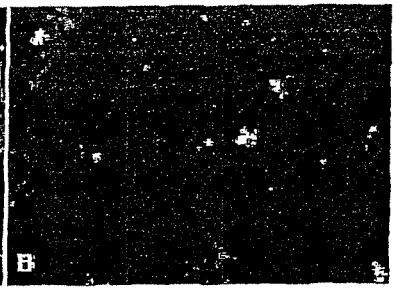
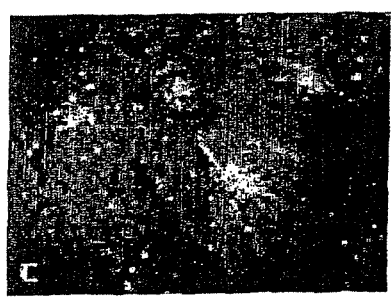
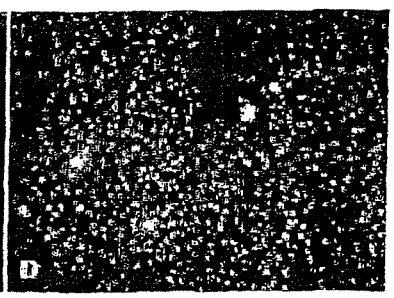
Fig. 18 C
Fig. 18D 19A  19B
19C  19D

SEQUENCE LISTING

```
<160> NUMBER OF SEQ ID NOS: 26

<210> SEQ ID NO 1
<211> LENGTH: 10
<212> TYPE: PRT
<213> ORGANISM: Mus musculus
```

-continued

```
<400> SEQUENCE: 1

Arg Ala Ser Ser Ser Val Asn Tyr Met His
1               5                   10

<210> SEQ ID NO 2
<211> LENGTH: 7
<212> TYPE: PRT
<213> ORGANISM: Mus musculus

<400> SEQUENCE: 2

Ala Thr Ser Asn Leu Ala Ser
1               5

<210> SEQ ID NO 3
<211> LENGTH: 9
<212> TYPE: PRT
<213> ORGANISM: Mus musculus

<400> SEQUENCE: 3

Gln Gln Trp Arg Thr Asn Pro Pro Thr
1               5

<210> SEQ ID NO 4
<211> LENGTH: 5
<212> TYPE: PRT
<213> ORGANISM: Mus musculus

<400> SEQUENCE: 4

Glu Tyr Thr Met His
1               5

<210> SEQ ID NO 5
<211> LENGTH: 17
<212> TYPE: PRT
<213> ORGANISM: Mus musculus

<400> SEQUENCE: 5

Gly Val Asn Pro Tyr Asn Asp Asn Thr Ser Tyr Ile Arg Lys Leu Gln
1               5                   10                  15

Gly

<210> SEQ ID NO 6
<211> LENGTH: 13
<212> TYPE: PRT
<213> ORGANISM: Mus musculus

<400> SEQUENCE: 6

Tyr Gly Gly Leu Arg Pro Tyr Tyr Phe Pro Met Asp Phe
1               5                   10

<210> SEQ ID NO 7
<211> LENGTH: 108
<212> TYPE: PRT
<213> ORGANISM: Artificial
<220> FEATURE:
<223> OTHER INFORMATION: VL of ESBA212

<400> SEQUENCE: 7

Ala Asp Ile Val Leu Thr Gln Ser Pro Ser Ser Leu Ser Ala Ser Val
1               5                   10                  15

Gly Asp Arg Val Thr Leu Thr Cys Arg Ala Ser Ser Ser Val Asn Tyr
            20                  25                  30

Met His Trp Tyr Gln Gln Arg Pro Gly Lys Pro Pro Lys Ala Leu Ile
        35                  40                  45
```

```
Tyr Ala Thr Ser Asn Leu Ala Ser Gly Val Pro Ser Arg Phe Ser Gly
     50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Trp Arg Thr Asn Pro Pro
                 85                  90                  95

Thr Phe Gly Gln Gly Thr Lys Leu Glu Val Lys Arg
            100                 105

<210> SEQ ID NO 8
<211> LENGTH: 108
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL of Framework 2.3

<400> SEQUENCE: 8

Ala Glu Ile Val Leu Thr Gln Ser Pro Ser Ser Leu Ser Ala Ser Val
1               5                  10                  15

Gly Asp Arg Val Thr Leu Thr Cys Arg Ala Ser Gln Gly Ile Arg Asn
                20                  25                  30

Glu Leu Ala Trp Tyr Gln Gln Arg Pro Gly Lys Ala Pro Lys Arg Leu
            35                  40                  45

Ile Tyr Ala Gly Ser Ile Leu Gln Ser Gly Val Pro Ser Phe Ser Gly
        50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                 85                  90                  95

Met Phe Gly Gln Gly Thr Lys Val Asp Ile Lys Arg
            100                 105

<210> SEQ ID NO 9
<211> LENGTH: 107
<212> TYPE: PRT
<213> ORGANISM: Mus musculus

<400> SEQUENCE: 9

Asp Ile Val Leu Thr Gln Ser Pro Ala Ile Leu Ser Ala Ser Pro Gly
1               5                  10                  15

Glu Lys Val Thr Leu Thr Cys Arg Ala Ser Ser Ser Val Asn Tyr Met
                20                  25                  30

His Trp Tyr Gln Gln Lys Pro Gly Ser Pro Pro Lys Ala Trp Ile Tyr
            35                  40                  45

Ala Thr Ser Asn Leu Ala Ser Gly Val Pro Asp Arg Phe Ser Ala Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Arg Thr Asn Pro Pro Thr
                 85                  90                  95

Phe Gly Ala Gly Thr Lys Leu Glu Leu Lys Arg
            100                 105

<210> SEQ ID NO 10
<211> LENGTH: 107
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL A

<400> SEQUENCE: 10

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Trp Thr
                85                  90                  95

Phe Gly Gln Gly Thr Lys Leu Thr Val Leu Gly
            100                 105

<210> SEQ ID NO 11
<211> LENGTH: 108
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL B

<400> SEQUENCE: 11

Glu Ile Val Leu Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Glu
            20                  25                  30

Leu Ala Trp Tyr Gln Gln Arg Pro Gly Lys Ala Pro Lys Arg Leu Ile
        35                  40                  45

Tyr Ala Gly Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                85                  90                  95

Met Phe Gly Gln Gly Thr Lys Val Asp Ile Lys Arg
            100                 105

<210> SEQ ID NO 12
<211> LENGTH: 109
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL C

<400> SEQUENCE: 12

Glu Ile Val Met Thr Gln Ser Pro Ala Thr Leu Ser Val Ser Pro Gly
1               5                   10                  15
```

```
Glu Ser Ala Ala Leu Ser Cys Arg Ala Ser Gln Gly Val Ser Thr Asn
            20                  25                  30

Val Ala Trp Tyr Gln Gln Lys Pro Gly Gln Ala Pro Arg Leu Leu Ile
        35                  40                  45

Tyr Gly Ala Thr Thr Arg Ala Ser Gly Val Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Ala Tyr Tyr Cys Gln Gln Tyr Lys His Trp Pro Pro
                85                  90                  95

Trp Thr Phe Gly Gln Gly Thr Lys Val Glu Ile Lys Arg
                100                 105
```

```
<210> SEQ ID NO 13
<211> LENGTH: 111
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL D

<400> SEQUENCE: 13
```

```
Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
                100                 105                 110
```

```
<210> SEQ ID NO 14
<211> LENGTH: 108
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL E

<400> SEQUENCE: 14
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Leu Thr His Tyr
            20                  25                  30

Leu Ala Trp Tyr Gln Gln Lys Pro Gly Gln Ala Pro Arg Leu Leu Ile
        35                  40                  45

Tyr Asp Thr Ser Lys Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Ser Ala Leu Tyr Tyr Cys Gln Gln Arg Asn Ser Trp Pro His
                85                  90                  95

Thr Phe Gly Gly Gly Thr Lys Leu Glu Ile Lys Arg
            100                 105
```

<210> SEQ ID NO 15
<211> LENGTH: 109
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL F

<400> SEQUENCE: 15

```
Ser Tyr Val Leu Thr Gln Pro Pro Ser Val Ser Val Ala Pro Gly Gln
1               5                   10                  15

Thr Ala Thr Val Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Arg Arg Val Glu Ala Gly
65                  70                  75                  80

Asp Glu Ala Asp Tyr Tyr Cys Gln Val Trp Asp Ser Ser Ser Asp His
                85                  90                  95

Asn Val Phe Gly Ser Gly Thr Lys Val Glu Ile Lys Arg
            100                 105
```

<210> SEQ ID NO 16
<211> LENGTH: 109
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VL G

<400> SEQUENCE: 16

```
Leu Pro Val Leu Thr Gln Pro Pro Ser Val Ser Val Ala Pro Gly Gln
1               5                   10                  15

Thr Ala Arg Ile Ser Cys Gly Gly Asn Asn Ile Glu Thr Ile Ser Val
                20                  25                  30

His Trp Tyr Gln Gln Lys Pro Gly Gln Ala Pro Val Leu Val Val Ser
            35                  40                  45

Asp Asp Ser Val Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly
            100                 105
```

<210> SEQ ID NO 17
<211> LENGTH: 122
<212> TYPE: PRT
<213> ORGANISM: Artificial
<220> FEATURE:

<223> OTHER INFORMATION: Synthetic peptide
<220> FEATURE:
<221> NAME/KEY: MISC_FEATURE
<223> OTHER INFORMATION: VH of ESBA212

<400> SEQUENCE: 17

```
Gln Val Gln Leu Val Gln Ser Gly Pro Glu Val Lys Lys Pro Gly Ala
1               5                   10                  15

Ser Val Lys Val Ser Cys Thr Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Tyr Asn Asp Asn Thr Ser Tyr Ile Arg Lys Leu
    50                  55                  60

Gln Gly Arg Val Thr Leu Thr Val Asp Arg Ser Ser Thr Ala Tyr
65                  70                  75                  80

Met Glu Leu Thr Ser Leu Thr Ser Asp Asp Thr Ala Val Tyr Tyr Cys
                85                  90                  95

Ala Arg Tyr Gly Gly Leu Arg Pro Tyr Tyr Phe Pro Met Asp Phe Trp
            100                 105                 110

Gly Gln Gly Thr Leu Val Thr Val Ser Ser
        115                 120
```

<210> SEQ ID NO 18
<211> LENGTH: 123
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VH of Framework 2.3

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Thr Ala Ser Gly Tyr Ser Phe Thr Gly Tyr
            20                  25                  30

Phe Leu His Trp Val Arg Gln Ala Pro Gly Gln Gly Leu Glu Trp Met
        35                  40                  45

Gly Arg Ile Asn Pro Asp Ser Gly Asp Thr Tyr Ala Gln Lys Phe Gln
    50                  55                  60

Asp Arg Val Thr Leu Thr Arg Asp Thr Ser Ile Gly Thr Val Tyr Met
65                  70                  75                  80

Glu Leu Thr Ser Leu Thr Ser Asp Asp Thr Ala Val Tyr Tyr Cys Ala
                85                  90                  95

Arg Val Pro Arg Gly Thr Tyr Leu Asp Pro Trp Asp Tyr Phe Asp Tyr
            100                 105                 110

Trp Gly Gln Gly Thr Leu Val Thr Val Ser Ser
        115                 120
```

<210> SEQ ID NO 19
<211> LENGTH: 122
<212> TYPE: PRT
<213> ORGANISM: Mus musculus

<400> SEQUENCE: 19

```
Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
```

-continued

```
                    20                  25                  30
Thr Met His Trp Val Lys Gln Ser His Gly Lys Ser Leu Glu Trp Ile
            35                  40                  45
Gly Gly Val Asn Pro Tyr Asn Asp Asn Thr Ser Tyr Ile Arg Lys Leu
        50                  55                  60
Gln Gly Lys Val Thr Leu Thr Val Asp Arg Ser Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Tyr Gly Gly Leu Arg Pro Tyr Tyr Phe Pro Met Asp Phe Trp
            100                 105                 110
Gly Gln Gly Thr Ser Val Thr Val Ser Ser
            115                 120

<210> SEQ ID NO 20
<211> LENGTH: 124
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VH H

<400> SEQUENCE: 20

Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ala His Val Leu Arg Phe Leu Glu Trp Leu Pro Asp Ala Phe Asp
            100                 105                 110
Ile Trp Gly Gln Gly Thr Leu Val Thr Val Ser Ser
            115                 120

<210> SEQ ID NO 21
<211> LENGTH: 108
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VH I

<400> SEQUENCE: 21

Glu Ile Val Leu Thr Gln Ser Pro Ser Ser Leu Ser Ala Ser Leu Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Ser Gln Ser Gly Val Pro Ser Arg Phe Arg Gly
```

```
                50                  55                  60
Ser Glu Ser Gly Thr Asp Phe Thr Leu Thr Ile Ser Asn Leu Gln Pro
 65                  70                  75                  80

Glu Asp Phe Ala Thr Tyr Tyr Cys Gln Gln Ser Tyr Arg Thr Pro Phe
                 85                  90                  95

Thr Phe Gly Pro Gly Thr Lys Val Glu Ile Lys Arg
            100                 105

<210> SEQ ID NO 22
<211> LENGTH: 123
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VH J

<400> SEQUENCE: 22

Val Gln Leu Val Gln Ser Gly Ala Glu Val Lys Lys Pro Gly Ala Ser
 1               5                  10                  15

Val Lys Val Ser Cys Thr Ala Ser Gly Tyr Ser Phe Thr Gly Tyr Phe
                20                  25                  30

Leu His Trp Val Arg Gln Ala Pro Gly Gln Gly Leu Glu Trp Met Gly
             35                  40                  45

Arg Ile Asn Pro Asp Ser Gly Asp Thr Ile Tyr Ala Gln Lys Phe Gln
 50                  55                  60

Asp Arg Val Thr Leu Thr Arg Asp Thr Ser Ile Gly Thr Val Tyr Met
 65                  70                  75                  80

Glu Leu Thr Ser Leu Thr Ser Asp Asp Thr Ala Val Tyr Tyr Cys Ala
                 85                  90                  95

Arg Val Pro Arg Gly Thr Tyr Leu Asp Pro Trp Asp Tyr Phe Asp Tyr
            100                 105                 110

Trp Gly Gln Gly Thr Leu Val Thr Val Ser Ser
            115                 120

<210> SEQ ID NO 23
<211> LENGTH: 122
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: VH K

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Gly Ile Ala Val Ala Gly Thr Gly Phe Asp Tyr Trp
```

```
                100                 105                 110
Gly Gln Gly Thr Leu Val Thr Val Ser Ser
            115                 120

<210> SEQ ID NO 24
<211> LENGTH: 250
<212> TYPE: PRT
<213> ORGANISM: Artificial
<220> FEATURE:
<223> OTHER INFORMATION: ESBA212

<400> SEQUENCE: 24

Ala Asp Ile Val Leu Thr Gln Ser Pro Ser Ser Leu Ser Ala Ser Val
1               5                   10                  15

Gly Asp Arg Val Thr Leu Thr Cys Arg Ala Ser Ser Ser Val Asn Tyr
            20                  25                  30

Met His Trp Tyr Gln Gln Arg Pro Gly Lys Pro Pro Lys Ala Leu Ile
        35                  40                  45

Tyr Ala Thr Ser Asn Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Trp Arg Thr Asn Pro Pro
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Val Gln Ser Gly Pro Glu Val Lys Lys Pro Gly Ala
    130                 135                 140

Ser Val Lys Val Ser Cys Thr Ala Ser Gly Tyr Thr Phe Thr Glu Tyr
145                 150                 155                 160

Thr Met His Trp Val Arg Gln Ala Pro Gly Gln Gly Leu Glu Trp Met
                165                 170                 175

Gly Gly Val Asn Pro Tyr Asn Asp Asn Thr Ser Tyr Ile Arg Lys Leu
            180                 185                 190

Gln Gly Arg Val Thr Leu Thr Val Asp Arg Ser Ser Ser Thr Ala Tyr
        195                 200                 205

Met Glu Leu Thr Ser Leu Thr Ser Asp Asp Thr Ala Val Tyr Tyr Cys
    210                 215                 220

Ala Arg Tyr Gly Gly Leu Arg Pro Tyr Tyr Phe Pro Met Asp Phe Trp
225                 230                 235                 240

Gly Gln Gly Thr Leu Val Thr Val Ser Ser
                245                 250

<210> SEQ ID NO 25
<211> LENGTH: 20
<212> TYPE: PRT
<213> ORGANISM: Artificial
<220> FEATURE:
<223> OTHER INFORMATION: linker

<400> SEQUENCE: 25

Gly Gly Gly Gly Ser Gly Gly Gly Ser Gly Gly Gly Gly Ser
1               5                   10                  15

Gly Gly Gly Ser
            20
```

```
<210> SEQ ID NO 26
<211> LENGTH: 11
<212> TYPE: PRT
<213> ORGANISM: Homo sapiens

<400> SEQUENCE: 26

Ala Ile Ile Gly Leu Met Val Gly Gly Val Val
1               5                   10
```

HUMANIZED ANTIBODIES AGAINST THE β-AMYLOID PEPTIDE

TECHNICAL FIELD

The present invention relates to the field of antibody technology, more specifically to the field of humanized antibodies against the beta-amyloid peptide.

BACKGROUND ART

Alzheimers disease (AD) is an age-related neurodegenerative disorder, which affected in 2006 26.6 million people. Forecasts predict that the prevalence will quadruple by 2050, by which time 1 in 85 persons worldwide will be living with the disease (Brookmeyer et al. (2007)). AD manifests itself as progressive cognitive deficits, such as memory loss and a decline in mental abilities.

Central in the pathogenesis of AD is the accumulation of beta-amyloid peptide (Abeta) in the brain. Abeta is a cleavage product of the amyloid precursor protein (APP) which is sequentially cleaved in the amyloidogenic pathway, first by β-secretase and then by γ-secretase. The resulting Abeta fragments are of variable size, whereas the 40 amino acid peptide (Abeta$_{40}$) is the most abundant species and the 42 amino acid peptide, the so-called Abeta$_{42}$, is believed to be the most harmful species. Abeta can accumulate in the extracellular space of the brain, where it aggregates in a multistep process to form neurotoxic oligomers and finally gives rise together with other substances to amyloid plaques, which are a typical hallmark of the Alzheimer disease.

A promising clinical immunologic approach for the treatment of Alzheimer's disease is passive immunization, in which antibodies against Abeta are administered to the subject in order to remove Abeta from the brain. Three different mechanisms for Abeta clearance through anti-Abeta antibodies have been proposed, which are not mutually exclusive: (1) the catalytic conversion of fibrillar Abeta to less toxic forms (Bard et al. (2000); Bacskai et al. (2001); Frenkel et al. (2000)); (2) the opsonization of Abeta deposits, leading to microglial phagocytosis (Bard et al. (2000); Bacskai et al. (2002); Frenkel et al. (2000); and (3) the promotion of the efflux of Abeta from the brain to the circulation (DeMattos et al. (2001)), the so-called peripheral sink hypothesis.

Mohajera et al. (2004) and Gaugler et al. (2005) of the University of Zurich have generated mouse antibodies against Abeta and studied the bioactivity of monoclonal murine anti-Abeta antibodies in vivo.

However, murine antibodies often result in immunogenicity when administrated to human beings. The elicited anti-globulin response limits the clinical utility of murine antibodies (Miller et al. (1983); Schroff et al. (1985)).

Hence, there is a need for new, non-immunogenic and effective antibodies for the treatment and/or diagnosis of Abeta-related disorders, specifically of Alzheimer's disease.

DISCLOSURE OF THE INVENTION

Hence, it is a general object of the invention to provide an antibody which specifically binds to Abeta, in particular to the C-terminal part of Abeta, and which is well tolerated by the human immune system.

In a first aspect, the invention provides an isolated antibody that selectively binds to Abeta in its C-terminal region, in particular between amino acids 30 to 40 (SEQ. ID. No. 26) and is humanized or fully human. The antibody displays a high affinity for both Abeta$_{42}$ and Abeta$_{40}$ and furthermore, does not substantially recognize amyloid precursor protein (APP) in vivo.

The advantage of the so-called humanized antibodies consists in their ability to elicit typically minimal or no response of the human immune system thus can be considered as being low or non-immunogenic upon human application. Therefore, contrary to murine antibodies, humanized antibodies are suitable for therapeutic purposes and clinical application.

The term "humanization" refers to well-established techniques which reduce the immunogenicity of xenogeneic antibodies. A humanized antibody is genetically engineered so that as little as possible non-human structure is present. One strategy is based on the grafting of complementarity determining regions (CDRs) of a xenogeneic antibody onto the variable light chain VL and variable heavy chain VH of a human acceptor framework. In another strategy, the framework of a xenogeneic antibody is mutated towards a human framework. In both cases, the retention of the functionality of the antigen-binding portions is essential. For said purpose, the three dimensional models of the parental sequences and various conceptual humanized products are analyzed, e.g. by the use of computer programs for molecular modelling which are well known to the skilled person. The analysis permits—among other—to identify the framework residues likely to be involved directly or indirectly in antigen binding. Often, a small number of donor framework residues are important for antigen binding because they enter in direct contact with the antigen or they affect the conformation of particular CDRs (Davies et al (1990); Chothia et al (1987)). Hence, if not already present, it is desirable to mutate the corresponding acceptor framework residues towards those donor framework residues which have been identified as being important for antigen binding. It may also be possible that humanized antibodies comprise residues which are found neither in the human germline repertoire in vivo, nor in the donor CDRs or even in the donor framework.

The degree of humanization of an antibody may be indicated by calculating the percentage of sequence identity of the framework of the humanized antibody to the original human acceptor framework that was used to generate the humanized antibody and that is obtainable from a human library. Preferably, the antibody of the invention comprises a framework with at least 60% identity, more preferably (in the following order) at least 75%, at least 80%, at least 85%, at least 90%, and most preferably 95% or even 100% identity to a framework obtainable of a human library. In the context of the present invention, the terms "complementarity determining regions" or "CDRs" refer to the complementarity determining regions of an antibody which consist of the antigen binding loops as defined by Kabat et al. (1991). CDR and framework residues of the present invention are determined according to the definition of Kabat (Kabat et al. (1987).

The term "antibody" as used herein refers to full-length antibodies, being for example monoclonal antibodies, and any antigen-binding fragment or single chain thereof with sufficient binding capacity for the selected antigen. Examples of antigen-binding fragments encompassed by the present invention include Fab fragments, F(ab')2 fragments, Fd fragments, Fv fragments; single domains or dAb fragments, isolated complementarity determining regions (CDR); a combination of two or more isolated CDRs which may optionally be joined by a synthetic linker and single chain variable fragments (scFv). "Full-length antibodies" include chimeric antibodies, in which an antigen-binding variable domain of one origin is coupled to a constant domain of a different origin, e.g. the variable domain Fv of a murine antibody to the constant domain Fc of a human antibody.

The above enumerated antibody fragments are obtained using conventional techniques known to those with skill in the art, and the fragments are screened for utility in the same manner as are intact antibodies.

In the present invention, the CDRs are derived from the monoclonal mouse antibody 22C4 (Mohajeri et al. (2002), J. Biol. Chem. 277, pp. 33012-33017 and Neurodegenerative Dis. 1 (2004), pp. 160-167). Said murine antibody is directed against the C-terminal part of Abeta, more specifically to an epitope within amino acids 30 to 40 (SEQ. ID. No. 26).

In a preferred embodiment, the antibody prevents the oligomerization of Abeta, particularly of $Abeta_{40}$ and/or $Abeta_{42}$, through binding to its target.

The present invention provides an antibody that comprises one or more complementarity determining regions (CDR) sequences with at least 80% identity to a sequence of the group consisting of SEQ ID: No. 1, SEQ ID: No. 2, SEQ ID: No. 3, SEQ ID: No. 4, SEQ ID: No. 5 and SEQ ID: No. 6.

As already mentioned, the CDRs of the present invention, namely SEQ ID: No. 1, SEQ ID: No. 2, SEQ ID: No. 3, SEQ ID: No. 4, SEQ ID: No. 5 and SEQ ID: No. 6, can be grafted into suitable acceptor frameworks. The term "frameworks" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface. Suitable acceptor frameworks are preferably those of immunoglobulin-derived antigen-binding polypeptides which are well-known in the art and include, but are not limited to VhH domains, V-NAR domains, Vh domains, Fab, scFv, Bis-scFv, Camel IG, IfNAR, IgG, Fab2, Fab3, minibody, diabodies, triabodies and tetrabodies (see Holliger, P. and Hudson, P. (2005), Nat. Biotechnol. 23(9), pp. 1126-1136). The framework sequence may also be a consensus sequence of a human framework sequence.

The antibody is selected from any class of immunoglobulins, including IgM, IgG, IgD, IgA and IgE, and isotype, and may comprise sequences for more than one class or isotype.

Preferably, the antibody comprises a framework with at least 60% identity, more preferably (in the following order) at least 75%, at least 80%, at least 85%, at least 90%, and most preferably 95% or even 100% identity to a framework obtainable of a human library.

The antibody of the present invention is a recombinant molecule, since the CDRs can be grafted upon a human framework and the resulting antibody comprises non-human CDRs and a human or essentially human framework. Alternatively, the antibody is derived form a non-human antibody and its framework is mutated towards a human antibody. Both alternatives are encompassed by the term "obtainable of a human library".

In one embodiment of the present invention, the antibody is a scFv antibody. The scFv can be either a full-length scFv comprising a VL and a VH domain which are linked by a short linker peptide, for example a linker comprising 1 to 4 repeats of the sequence GGGGS, preferably a $(GGGGS)_4$ peptide (SEQ ID No. 25), or a linker as disclosed in Alfthan et al. (1995) Protein Eng. 8:725-731, or simply a VL or a VH domain, which has sufficient binding capacity for the selected antigen. The linkage of VL and VH can be in either orientation, VL-linker-VH or VH-linker-VL.

In one embodiment, the framework of the scFv is stable and soluble in a reducing environment. These characteristics can be identified by the so-called Quality control system, as disclosed in WO01/48017. The stability of said antibodies preferably is at least half as good as the stability of the particularly stable lambda graft, more preferably at least as good as the lambda graft, and most preferably better than the lambda graft. Worn et al. (2000) describe the onset of denaturation of the lambda graft to be around 2.0M GdnHCl. It has been shown that scFvs which perform well in the Quality control system are also stable and soluble under oxidizing conditions. In a preferred embodiment, the solubility of the antibody of the invention as measured according to the method of Atha and Ingham (1981) is at least 5 mg/ml, more preferably at least 10 mg/ml, and most preferably at least 20 mg/ml.

In a further preferred embodiment, the antibody comprises a variable light chain fragment ($V_L$) framework which is identical or derived from the framework sequences comprised in the sequences of the group consisting of SEQ ID. No. 7, SEQ ID. No. 8, SEQ ID. No. 10, SEQ ID. No. 11, SEQ ID. No. 12, SEQ ID. No. 13, SEQ ID. No. 14, SEQ ID. No. 15 and SEQ ID. No. 16. In case of a derived sequence, said sequence shows at least 60% identity, more preferably (in the following order) at least 75%, at least 80%, at least 85%, at least 90%, and most preferably 95% or even 100% identity to a sequence of the group consisting of SEQ ID. No. 7, SEQ ID. No. 8, SEQ ID. No. 10, SEQ ID. No. 11, SEQ ID. No. 12, SEQ ID. No. 13, SEQ ID. No. 14, SEQ ID. No. 15 and SEQ ID. No. 16.

In a further preferred embodiment, the antibody of the present invention comprises a variable heavy chain fragment ($V_H$) framework which is identical or derived from the framework sequences comprised in the sequences of the group consisting of SEQ ID. No. 17, SEQ ID. No. 18, SEQ ID. No. 20, SEQ ID. No. 21, SEQ ID. No. 22 and SEQ ID. No. 23. In case of a derived sequence, said sequence shows at least 60% identity, more preferably (in the following order) at least 75%, at least 80%, at least 85%, at least 90%, and most preferably 95% or even 100% identity to a sequence of the group consisting of SEQ ID. No. 17, SEQ ID. No. 18, SEQ ID. No. 20, SEQ ID. No. 21, SEQ ID. No. 22 and SEQ ID. No. 23.

Sequences SEQ ID. No. 8, SEQ ID. No. 10, SEQ ID. No. 11, SEQ ID. No. 12, SEQ ID. No. 13, SEQ ID. No. 14, SEQ ID. No. 15 SEQ ID. No. 16, SEQ ID. No. 20, SEQ ID. No. 21, SEQ ID. No. 22 and SEQ ID. No. 23 are disclosed in WO03/097697. These framework sequences stem from human immunoglobulin origin and their solubility and stability characteristics under reducing conditions have been proven in the so-called Quality control system, as disclosed in WO01/48017.

More preferably, the antibody comprises a VH fragment of SEQ ID: No. 7 and a VL sequence of SEQ ID: No. 17.

Most preferably, the antibody has a sequence being at least 60% identical, more preferably at least 75%, 80%, 90%, 95% identical to Seq. ID. No. 24. In a most preferred embodiment, the antibody of the present invention is structurally defined by Seq. ID. No. 24. In said antibody, SEQ ID: No. 7 and SEQ ID: No. 17 are linked through a $(GGGGS)_4$ linker. The resulting scFv antibody was named ESBA212.

It will be understood by one of ordinary skill in the art that the sequences of the invention may be altered such that they vary in amino acid sequence from the here disclosed sequences, while retaining the selective binding ability to the C-terminal part of Abeta. Hence, neither the framework nor the CDR regions of the humanized antibody need to correspond precisely to the donor CDR or acceptor framework.

Alterations therein can be created by introducing one or more nucleotide substitutions, additions or deletions into the nucleotide sequence of the antibody by standard techniques, such as site-directed mutagenesis and PCR-mediated mutagenesis. Such mutations can be introduced for different purposes, e.g. for improving binding, solubility or stability characteristics of the antibody. The antibodies of the invention may also comprise conservative amino acid substitutions at one or more non-essential amino acid residues. In another embodiment, mutations may be introduced randomly along all or part of the coding sequence such as by saturation mutagenesis, and the resultant mutants can be screened for their ability to bind to the desired target.

The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, which is well known to those skilled in the art. The identities referred to herein are to be determined by using the BLAST programs (Basic Local Alignment Search Tools; see Altschul, S. F., Gish, W., Miller, W., Myers, E. W. & Lipman, D. J. (1990) "Basic local alignment search tool." J. Mol. Biol. 215:403-410) accessible in Internet. BLAST protein searches can be performed with the XBLAST program, score=50, wordlength=3 to compare amino acid sequences to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The protein sequences of the present invention can further be used as a "query sequence" to perform a search against public databases to, for example, identify related sequences. Such searches can be performed using the aforementioned XBLAST programs (version 2.0).

The humanized or fully human antibodies encompassed by the present invention show the following characteristics:

(i) Binding to the C-terminus of Abeta, thus binding to both $Abeta_{40}$ and $Abeta_{42}$ with a high and substantially identical affinity;

(ii) Displaying a high affinity for oligomeric and monomeric forms of Abeta;

(iii) Not substantially recognizing amyloid precursor protein (APP) in vivo;

(iv) Having a solubility of at least 5 mg/ml, preferably at least 10 mg/ml, and more preferably at least 20 mg/ml; and (v) Showing low or no immunogenicity upon human application.

Further, the antibody preferably shows at least one, more preferably more than one, most preferred all of the following characteristics:

(vi) Mediating the uptake of fibrillar Abeta by microglia;

(vi) Binding beta-amyloid plaques;

(vii) Removing beta-amyloid plaques in the brain and/or preventing the formation of amyloid plaques in the brain;

(viii) Decreasing Abeta toxicity and associated vulnerability of neurons to excitotoxic events produced by seizures;

(ix) Crossing the blood brain barrier; and/or (x) Substantially restoring normal behavior;

(xi) Removing beta-amyloid fibrils in the brain and/or preventing the formation of amyloid fibrils in the brain.

The antibody of the present invention does not substantially recognize amyloid precursor protein (APP) in vivo.

Preferably, the binding affinity to Abeta is a factor of at least two, more preferably at least 5, even more preferably at least 10, particularly preferably at least 50, and most preferably at least 100 times higher when compared to the binding affinity for APP.

Thus, upon administration of the antibody to a subject, APP does not compete with Abeta for binding and the antibody does not interfere with the biology of uncleaved APP. This feature is e.g. particularly interesting for diagnostic purposes and/or medical treatment of neurological disorders associated with abnormal accumulation and/or deposition of Abeta in the central nervous system.

The term "neurological disorder" as used herein includes—but is not limited to—Alzheimer's disease, mild cognitive impairment, aphasia, fronto-temporal dementia, Lewy-body disease, Parkinson's disease, Pick's disease, Binswanger's disease, cerebral amyloid angiopathy, Down's syndrome, multi-infarct dementia, Huntington's Disease, Creutzfeldt-Jakob Disease, AIDS dementia complex, depression, anxiety disorder, phobia, Bell's Palsy, epilepsy, encephalitis, multiple sclerosis; neuromuscular disorders, neurooncological disorders, brain tumors, neurovascular disorders including stroke, neuroimmunological disorders, neurootological disease, neurotrauma including spinal cord injury, pain including neuropathic pain, pediatric neurological and neuropsychiatric disorders, sleep disorders, Tourette syndrome, mild cognitive impairment, vascular dementia, multi-infarct dementia, cystic fibrosis, Gaucher's disease other movement disorders, glaucoma and disease of the central nervous system (CNS) in general. More preferably, the antibody of the present invention is used in the treatment, prevention, delay of progression or diagnosis of Alzheimer's disease, stroke, neurotrauma and glaucoma.

In another aspect the antibody of the present invention is chemically modified. Chemical modifications may change properties of the antibody such as stability, solubility, antigen-binding specificity or affinity, in vivo half life cytotoxicity, and tissue penetration ability. Chemical modifications are well known to the skilled person. A preferred chemical modification of the antibody of the present invention is PEGylation.

In one embodiment, the antibody is conjugated to a therapeutic agent, e.g. a toxin or a chemotherapeutic compound. The antibody may be conjugated to a radioisotope, such as—without being limited to—$^{212}Bi$, $^{125}I$, $^{131}I$, $^{90}Y$, $^{67}Cu$, $^{212}Bi$, $^{212}At$, $^{211}Pb$, $^{47}Sc$, $^{109}Pd$, and $^{188}Re$, e.g. for immunotherapy.

In a further embodiment, the antibody of the present invention may be linked to a label. Said label may allow for colorimetric detection of the antibody. Alternatively, the antibody is radiolabelled. Most preferably, the radiolabel is $^{64}Cu$.

Another object of the present invention is to provide a diagnostic or scientific tool comprising the antibody disclosed herein.

The antibody of the present invention may be used in diagnosis or screening a subject for amyloidosis or Alzheimer's disease or determining a subject's risk for developing amyloidosis or Alzheimer's disease.

In a further embodiment, the invention furthermore encompasses a diagnostic method comprising the step of administering an effective amount of an antibody of the present invention to a subject, preferably a mammal. The method further comprises the step of detecting the label.

In a further embodiment, the present invention encompasses an immunoassay comprising the antibody described herein, wherein the assay may be an in vivo or an in vitro immunoassay. The antibody may be used in liquid phase or bound to a solid phase. Examples of such immunoassays include radioimmunoassays (RIA), flow cytometry, Western Blots and microarrays.

Furthermore, the invention encompasses a test kit comprising the antibody disclosed herein.

In a preferred embodiment, the antibody of the present invention mediates the uptake of fibrillar Abeta by microglia, thereby reducing Abeta levels in vivo.

In a further preferred embodiment, the antibody of the present invention improves upon administration of an effective amount the cognitive behavior and rescues the number of immature neurons in subjects with Alzheimer's disease.

Moreover, the present invention encompasses a a pharmaceutical composition to treat, prevent and/or delay the progression of a neurological disorder or amyloidosis characterized by abnormal accumulation and/or deposition of Abeta in the central nervous system, in particular Alzheimer's disease, comprising the antibody disclosed herein.

In a further embodiment, the invention provides a method of manufacture of a pharmaceutical composition for the treatment, prevention, and/or delay of progression of the above mentioned neurological disorders, preferably Alzheimer's disease, comprising the step of combining the antibody disclosed herein with at least one suitable pharmaceutical carrier.

Preferably, the pharmaceutical compositions disclosed herein prevent and/or reduce the effect of Abeta accumulation in the brain of a subject.

The antibody can be administered in combination with a pharmaceutically acceptable carrier or in combination with one or more further effective agents. Effective agents may be small organic molecules and/or anti-Abeta antibodies.

The antibody and/or pharmaceutical compositions disclosed herein may be administered in different ways, e.g. intravenously, intraperitoneally, intranasally, subcutaneously, intramuscularly, topically or intradermally, intracranially, intrathecally into the cerebrospinal fluid. Preferred kinds of application are (in this sequence) intranasal, subcutaneous, intravenous, intrathecally into the cerebrospinal fluid and intracranial administration.

Typically used formulations are known to the skilled person. For example, aerosol formulations such as nasal spray formulations include purified aqueous or other solutions of the active agent with preservative agents and isotonic agents. Such formulations are preferably adjusted to a pH and isotonic state compatible with the nasal mucous membranes.

Furthermore, co-administration or sequential administration of other agents may be desirable. Preferably, the antibody is present in an amount sufficient to restore normal behavior and/or cognitive properties in case of Alzheimer's disease.

In a further embodiment, the present invention provides methods for the treatment, prevention and/or delay of progression of a neurological disease as mentioned above, comprising the step of administering an effective amount of an antibody of the present invention to a subject in need thereof.

Another object of the present invention is to provide a method for passive immunization of a mammal, comprising the step of administering the antibody disclosed herein to a mammal. Preferably, the passive immunization is performed within the scope of an anti-Abeta immunotherapy.

In another embodiment, the invention features isolated nucleic acid sequence comprising a sequence encoding the amino acid sequences encompassed by the present invention. Said nucleic acids may be either DNA or RNA and be either single stranded or double stranded.

Furthermore, the present invention provides a cloning or expression vector containing a DNA sequence coding for a polypeptide, most preferably the antibody, of the present invention.

In addition, a suitable host cell harbouring the vector and/or the nucleic acid sequence comprising a sequence coding for the here disclosed amino acid sequences, is provided. This can be a prokaryotic or eukaryotic cell, in particular an *E. coli*, yeast, plant, insect or a mammalian cell.

The antibody of the present invention may be generated using routine techniques in the field of recombinant molecular biology. Knowing the sequences of the polypeptides, the person skilled in the art may generate corresponding cDNAs coding for the polypeptides by gene synthesis.

In another embodiment, a method for the production of the antibody of the present invention is provided, comprising culturing of the host cell transformed with the DNA encoding said antibody under conditions that allow the synthesis of said antibody, and recovering said molecule from said culture. Preferably, said method provides an scFv antibody purified from *E. coil* inclusion bodies or from the *E. coli* periplasm, if the scFv construct used comprises a signal sequence that directs the polypeptide to the periplasm. It may be necessary to include a renaturate step to refold the antibody to a functional molecule.

In a further embodiment, the invention provides a method of treatment comprising the step of administering to a subject in need thereof a therapeutically effective amount of a polynucleotide, vector or host cell as described herein.

In a second aspect, the present invention provides a method of diagnosis comprising the steps of:
(i) Labelling an antibody;
(ii) Administering an effective dose of said antibody intranasally or systemically to a subject; and
(iii) Detecting the concentration and/or presence of the labelled antibody in body parts of the subject.

The antibody is preferably the humanized antibody against the epitope formed within the amino acids 30 to 40 of Abeta of the present invention, preferably a single chain antibody (scFv). In a preferred embodiment, the antibody is labelled with a positron emitting isotope, most preferably $^{64}$Cu.

The term "effective dose" as used herein refers to an amount sufficient to achieve or at least partially achieve the desired effect, e.g. a detectable signal. Amounts effective for this use will depend upon the detective strength of the label, body mass of the subject and the extent of the area to be examined.

Preferably, the subject is a mammal; more preferably, the subject is a human being.

The medical imaging technique Positron emission tomography (PET) which produces a three-dimensional image of body parts is based on the detection of radiation from the emission of positrons. Typically, a biomolecule is radioactively labeled, e.g. it incorporates a radioactive tracer isotope. Upon administration of the labeled biomolecule to the subject, typically by injection into the blood circulation, the radioactively labeled biomolecule becomes concentrated in tissues of interest. The subject is then placed in the imaging scanner, which detects the emission of positrons.

In one embodiment, a $^{64}$Cu labelled antibody is administered to a subject and step iii) is performed by placing the subject in an imaging scanner and detecting the emission of positrons.

The invention thus encompasses a method for PET imagining, comprising the step of administering a $^{64}$Cu-labelled antibody of the present invention to a subject.

The sequences of the present invention are the following:

SEQ. ID. No. 1: CDR1 of VL
RASSSVNYMH

SEQ. ID. No.2: CDR2 of VL
ATSNLAS

SEQ. ID. No.3: CDR3 of VL
QQWRTNPPT

SEQ. ID. No. 4: CDR1 of VH
EYTMH

SEQ. ID. No. 5: CDR2 of VH
GVNPYNDNTSYIRKLQG

SEQ. ID. No. 6: CDR3 of VH
YGGLRPYYFPMDF

SEQ. ID. No. 7: VL of ESBA212
ADIVLTQSPSSLSASVGDRVTLTCRASSSVNYMHWYQQRPGKPPKALIYA
TSNLASGVPSRFSGSGSGTEFTLTISSLQPEDVAVYYCQQWRTNPPTFGQ
GTKLEVKR

SEQ. ID. No. 8: VL of Framework 2.3
AEIVLTQSPSSLSASVGDRVTLTCRASQGIRNELAWYQQRPGKAPKRLIY
AGSILQSGVPSFSGSGSGTEFTLTISSLQPEDVAVYYCQQYYSLPYMFGQ
GTKVDIKR SEQ. ID. No. 9: VL of 22C4
DIVLTQSPAILSASPGEKVTLTCRASSSVNYMHWYQQKPGSPPKAWIYAT
SNLASGVPDRFSASGSGTSYSLTISRVEAEDAATYYCQQWRTNPPTFGAG
TKLELKR SEQ. ID. No. 10: VL A
EIVMTQSPSTLSASVGDRVIITCRASQSISSWLAWYQQKPGKAPKLLIYK
ASSLESGVPSRFSGSGSGAEFTLTISSLQPDDFATYYCQQYKSYWTFGQG
TKLTVLG;

SEQ. ID. No. 11: VL B
EIVLTQSPSSLSASVGDRVTLTCRASQGIRNELAWYQQRPGKAPKRLIYA
GSILQSGVPSRFSGSGSGTEFTLTISSLQPEDVAVYYCQQYYSLPYMFGQ
GTKVDIKR;

SEQ. ID. No. 12: VL C
EIVMTQSPATLSVSPGESAALSCRASQGVSTNVAWYQQKPGQAPRLLIYG
ATTRASGVPARFSGSGSGTEFTLTINSLQSEDFAAYYCQQYKHWPPWTFG
QGTKVEIKR;

SEQ. ID. No. 13: VL D
QSVLTQPPSVSAAPGQKVTISCSGSTSNIGDNYVSWYQQLPGTAPQLLIY
DNTKRPSGIPDRFSGSKSGTSATLGITGLQTGDEADYYCGTWDSSLSGVV
FGGGTKLTVLG;

SEQ. ID. No. 14: VL E
EIVLTQSPATLSLSPGERATLSCRASQTLTHYLAWYQQKPGQAPRLLIYD
TSKRATGVPARFSGSGSGTDFTLTISSLEPEDSALYYCQQRNSWPHTFGG
GTKLEIKR;

SEQ. ID. No. 15: VL F
SYVLTQPPSVSVAPGQTATVTCGGNNIGSKSVHWYQQKPGQAPVLVVYDD
SDRPSGIPERFSGSNSGNTATLTIRRVEAGDEADYYCQVWDSSSDHNVFG
SGTKVEIKR;

SEQ. ID. No. 16: VL G
LPVLTQPPSVSVAPGQTARISCGGNNIETISVHWYQQKPGQAPVLVVSDDS
VRPSGIPERFSGSNSGNTATLTISRVEAGDEADYYCQVWDSSSDYVVFGGG
TKLTVLG;

SEQ. ID. No. 17: VH of ESBA212
QVQLVQSGPEVKKPGASVKVSCTASGYTFTEYTMHWVRQAPGQGLEWMGG
VNPYNDNTSYIRKLQGRVTLTVDRSSSTAYMELTSLTSDDTAVYYCARYG
GLRPYYFPMDFWGQGTLVTVSS

SEQ. ID. No. 18: VH of Framework 2.3
QVQLVQSGAEVKKPGASVKVSCTASGYSFTGYFLHWVRQAPGQGLEWMGR
INPDSGDTYAQKFQDRVTLTRDTSIGTVYMELTSLTSDDTAVYYCARVPR
GTYLDPWDYFDYWGQGTLVTVSS SEQ. ID. No. 19: VH of 22C4
QVQLQQSGPELVKPGASVKISCKTSGYTFTEYTMHWVKQSHGKSLEWIGG
VNPYNDNTSYIRKLQGKVTLTVDRSSSTAYMELRSLTSEDSAVYFCARYG
GLRPYYFPMDFWGQGTSVTVSS SEQ. ID. No. 20: VH H
QVQLVQSGGGLVQPGGSLRLSCAASGFTFSSYAMSWVRQAPGKGLEWVSA
ISGSGGSTYYADSVKGRFTISRDNSKNTLYLQMNSLRAEDTAVYYCAAHV
LRFLEWLPDAFDIWGQGTLVTVSS SEQ. ID. No. 21: VH I
EIVLTQSPSSLSASLGDRVTITCRASQSISSYLNWYQQKPGKAPKLLIYA
ASSSQSGVPSRFRGSESGTDFTLTISNLQPEDFATYYCQQSYRTPFTFGP
GTKVEIKR SEQ. ID. No. 22: VH J
VQLVQSGAEVKKPGASVKVSCTASGYSFTGYFLHWVRQAPGQGLEWMGRI
NPDSGDTIYAQKFQDRVTLTRDTSIGTVYMELTSLTSDDTAVYYCARVPR
GTYLDPWDYFDYWGQGTLVTVSS SEQ. ID. No. 23: VH K
EVQLVESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKDA
GIAVAGTGFDYWGQGTLVTVSS SEQ. ID. No. 24: ESBA212
(The CDRs according to Kabat are underlined, and
the linker sequence is shown in italics).
ADIVLTQSPSSLSASVGDRVTLTC<u>RASSSVNYMH</u>WYQQRPGKPPKALIYA
<u>TSNLAS</u>GVPSRFSGSGSGTEFTLTISSLQPEDVAVYYC<u>QQWRTNPPT</u>FGQ
GTKLEVKR*GGGGSGGGGSGGGGSGGGGS*QVQLVQSGPEVKKPGASVKVSC
TASGYTFT<u>EYTMH</u>WVRQAPGQGLEWMG<u>GVNPYNDNTSYIRKLQG</u>RVTLTV
DRSSSTAYMELTSLTSDDTAVYYCAR<u>YGGLRPYYFPMDF</u>WGQGTLVTVSS SEQ. ID. No. 25: linker
GGGGSGGGGSGGGGSGGGGS SEQ. ID. No. 26: Abeta$_{30-40}$ epitope
AIIGLMVGGVV Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

It is understood that the various embodiments, preferences and ranges may be combined at will. Further, depending of the specific embodiment, selected definitions, embodiments or ranges may not apply.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 shows a sequence comparison of the light chain variable region of ESBA212 (SEQ ID NO: 7) with the VL of ESBATech's framework 2.3 (SEQ ID NO: 8) onto which the Abeta specific CDRs from 22C4 were grafted.

In FIG. 2, a sequence comparison of the variable heavy chain VH of ESBA212 (SEQ ID NO: 17) with the VH of ESBATech's framework 2.3 (SEQ ID NO: 18) is illustrated.

FIG. 3 depicts a sequence alignment of VH of ESBA212 (SEQ ID NO: 17) with the VH of the original VH from the mouse 22C4 antibody (SEQ ID NO: 19).

FIG. 4: shows a sequence alignment of the VH of ESBA212 (SEQ ID NO: 17), 22C4 (SEQ ID NO: 19) and framework (SEQ ID NO: 18).

FIG. 5. shows the results of ex vivo labeling of plaques in AD mouse models by ESBA212. Either paraffin sections or cryosections (non-fixed and post-fixed) were used. FIG. 5A: mouse model SwePS1, paraffin section; FIG. 5B: mouse model SwePS1, cryo section; FIG. 5C: mouse model SweArc, paraffin section; FIG. 5D: mouse model SweArc, cryo section.

FIG. 6. depicts the results of ex vivo labeling of plaques in human AD brains by ESBA212. Either paraffin sections or cryosections (non-fixed and post-fixed) were used. FIG. 6A: Paraffin section; FIG. 6B: cryo, acetone fixed; FIG. 6C: cryo, untreated; FIG. 6D: cryo; acetone fixed, boiled for 10 min in citrate buffer.

FIG. 7. shows the ex vivo staining of amyloid plaques by ESBA212 (FIG. 7A) and Thioflavine S (FIG. 7B) on brain sections of SwePS1 mice.

FIG. 8: illustrates the results of size exclusion chromatography of ESBA212 bound to FITC labeled Abeta42 monomers (FIG. 8A) and in FIG. 8B a control wherein the framework FW2.3 was incubated with FITC labeled Abeta42 monomers.

FIG. 9. shows two Abeta42 immunoblots using brain homogenates of transgenic SwePS1 mice (FIG. 9A; lane 1: ESBA212, lane 2: 6E10) and ADDLs (FIG. 9B; lane 1: Fw 2.3, lane 2: ESBA212, lane 3: 6E10) as antigens. ESBA212 recognizes predominantly monomers and weaker trimers.

FIG. 15: Mean serum concentrations of ESBA212 over time after a single intravenous or intraperitoneal injection.

FIG. 16: Detection of bound ESBA212 after intranasal (FIG. 16A) or intravenous (FIG. 16B) application. ESBA212 binds to amyloid plaques in the brain independent of the chosen route of application.

FIG. 17: Detection of bound ESBA212 in SwePS1 mouse brains after intranasal application (FIG. 17A) and thioflavine S staining (FIG. 17D) confirming that ESBA212 binds to amyloid plaques.

FIG. 18: Ex vivo labelling of amyloid plaques by $^{64}$Cu-ESBA212 (FIGS. 18B and D) compared to ESBA212 (FIGS. 18A and C). FIGS. 18A and B show paraffin sections, whereas FIGS. 18 C and D show cryo sections.

FIG. 19A: ESBA212 after 24 h; FIG. 19B: ESBA212 after 48 h; FIG. 19C: Cu-ESBA212 after 24 h; and FIG. 19D: Cu-ESBA212 after 48 h.

FIG. 21: Further intranasal application similar to FIG. 16A showing Aβ-staining on fixed SwePS1 mouse brain slices of an animal perfused 1 h after intranasal treatment with 200 μg of ESBA212.

FIG. 22: Brain Aβ 40 and 42 levels in APPswe/PS1ΔE9 mice treated with PBS, 22c4 IgG and ESBA212 for 3 months.

FIG. 23: Paraffin sections of treated APPswe/PS1ΔE9 mice stained with 6E10 and evaluated using ImageJ software.

MODES FOR CARRYING OUT THE INVENTION

Example 1

Generation of ESBA212

Figures 10, 10A:
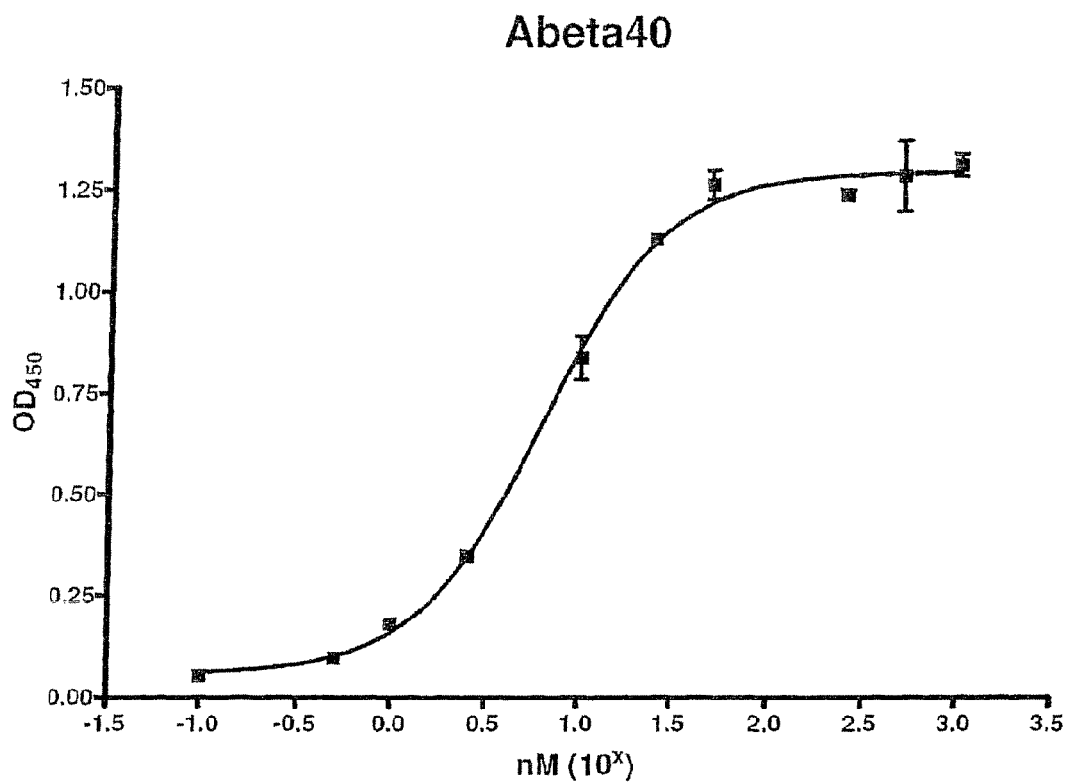
FIG. 10: Determination of affinity of ESBA212 by ELISA (FIG. 10A: for Abeta40; affinity constant: 6.26 nM.
Figure 10B:
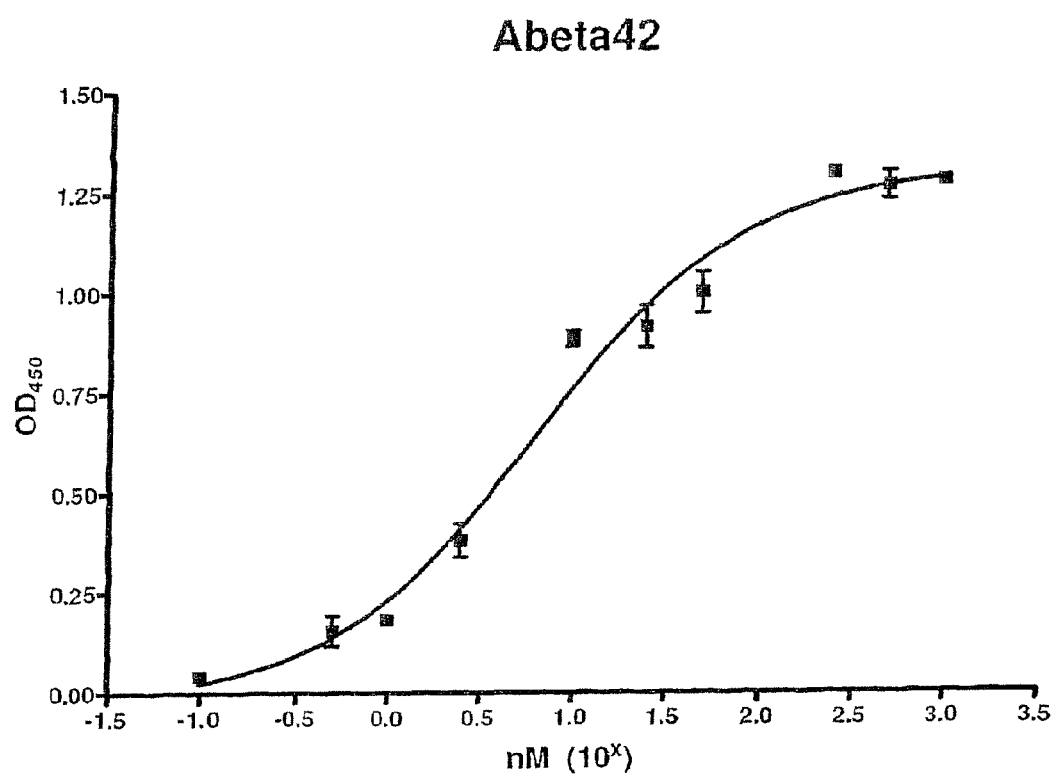
FIG. 10B for Abeta42; affinity constant: 6.31 nM).

The antigen-binding portions of the single chain antibody ESBA212 emanate from the murine antibody 22C4, identified by the University of Zurich. The Abeta-specific mouse IgG antibody 22C4 was generated by immunizing mice with Abeta$_{30-42}$ and is thus directed against the C-terminus of Abeta. The cloning of the VL and the VH domains was done by RT-PCR according to Burmester and Plückthun (2001). Briefly, the mRNA was derived from hybridoma cells producing the antibody 22C4. An RT-PCR using the primers described by Burmester and Plückthun was performed to amplify the VL and VH domains. The two domains were assembled by a SOE-PCR (splicing by overlap extension). Then the amplified single chain variable fragment (scFv) was digested by SfiI, cloned into a suitable expression vector and sequenced. Thus a mouse scFv fragment was obtained which kept its specificity for Abeta$_{42}$. Said scFv was humanized leading to the single chain antibody ESBA212 (see FIGS. 1 to 4 for sequence comparisons. FIGS. 1 and 2 show a sequence alignment of ESBA212 with the framework 2.3 onto which the Abeta specific CDRs from 22C4 were grafted.).

Plasmids encoding ESBA212 were introduced into a suitable *E. coli* strain (e.g. BL21) and expressed as inclusion bodies. Functional single chain antibodies were obtained by refolding of inclusion bodies and subsequent purification by gel filtration.

Example 2

Binding to Amyloid Plaques on Tissue Sections

In order to test whether the scFv ESBA212 was able to recognise Abeta, ex vivo immunostainings of brain tissues containing amyloid plaques were performed. Therefore, brain tissue sections from various transgenic mice (SweArc, SwePS1) that express human APP leading to the formation of Abeta plaques and brain sections from human Alzheimer's patients were used.

ESBA212 reacted with amyloid plaques on both cryo and paraffin sections from mice independent of the Alzheimer's mouse model used (FIG. 5). ESBA212 also stained plaques on fixed human Alzheimer's tissue (FIG. 6A). Especially around the vessels a strong staining could be observed that is known as amyloid angiopathy. Amyloid angiopathy refers to the deposition of beta-amyloid in the small and mid-sized vessels of the cerebral cortex and the leptomeninges. However, ESBA212 does not bind to amyloid plaques on human cryo sections, neither on non-fixed (FIG. 6B) nor on post-fixed (FIG. 6C, D) sections.

The different results between the human and rodent sections may be explained in that transgenic mice overexpress human APP and therefore the abundance of different plaques species might be different compared to humans. Güntert et al. (2006) described that there is an ultrastructural difference between diffuse plaques in a transgenic mouse model and human AD brains. In the mouse brain compact plaques of different sizes represent the majority. In the cortex and the hippocampus of human AD patients this plaque type occurs at only 10%, whereas cored plaques predominate (~90%) (Güntert et al., 2006). Because of these observed differences the C-terminus might be accessible in brains of transgenic mice but not in brains of AD patients. The fixation of human brain tissue might alter the conformation of the amyloid plaques in a way that the otherwise buried C-terminal epitope is exposed and gets accessible for ESBA212.

FIG. 7 shows the specific binding of ESBA212 to amyloid plaques on SwePS1 brain sections as the staining pattern of ESBA212 coincided with the pattern of thioflavine S which is a standard fluorescent stain that specifically binds to amyloid protein deposits.

Example 3

Binding to Abeta42 Monomers

It could be shown by size exclusion chromatography that ESBA212 bound to FITC-labelled Abeta 42. ESBA212 was co-incubated with FITC-Abeta42 and loaded onto a column. ESBA212 and FITC-Abeta42 were eluted together (FIG. 8A) as the peak for ESBA212 and the one for FITC-Abeta42 overlapped exactly and also showed a size shift of 5 kDa compared to ESBA212 alone (data not shown), therefore representing bound FITC-Abeta42 (5 kDa). However, when FITC-Abeta42 was incubated with the framework FW2.3, which contains the same framework region as ESBA212 but no Abeta-specific CDRs, there were two clearly distinct peaks observed one for the scFv and a second one for FITC-Abeta42 (FIG. 8B).

Example 4

Binding to Different Abeta42 Conformations

Abeta42 immunoblots were performed to further characterize the specificity of ESBA212. Therefore, brain homogenates of SwePS1 mice as well as in vitro generated ADDLs (amyloid beta-derived diffusible ligands, protocol by Klein) were separated on a SDS gel and transferred to a membrane. ESBA212 and 6E10 (Abeta-specific IgG as control) were used to detect Abeta. The control antibody 6E10 recognised Abeta42 monomers, beta-stubs, trimers and also full-length APP. However, ESBA212 recognised predominantly Abeta42 monomers (FIG. 9).

Example 5

In Vitro Characterization of Affinity

The binding properties of ESBA212 were tested in an ELISA where Abeta40 and Abeta42, respectively, were used as antigens. 96-well plates were coated with 5 ug/ml neutravidin in dilution buffer (PBS/0.01% BSA/0.2% Tween-20) and incubated overnight at 4° C. The plates were then washed 3 times with TBS/0.005% Tween-20. Biotinylated Abeta40 or Abeta42 (1 ug/ml in dilution buffer) were added to each well and the plate incubated for 15 minutes at room temperature. Plates were washed as above and non-specific binding sites were blocked by addition of dilution buffer. The plates were incubated for another 1.5 hours at room temperature while shaking. After washing the prepared ESBA212 dilutions from 0 to 500 nM were added in triplicates to the wells and incubated for 1 hour at room temperature (RT) while shaking. Plates were washed and ESBA212 was detected by a purified rabbit polyclonal anti-ESBA212 antibody (1:10000 in dilution buffer) for 1 hour at RT. After washing a horseradish peroxidase-labelled anti-rabbit IgG (1:4000 in dilution buffer) was used to detect the previously bound rabbit antibodies and POD was used as substrate. The reaction was stopped by addition of 1 M HCl and the absorption read at 450 nm.

From the measured ESBA212 curve an EC50 could be calculated. For ESBA212 the EC50 was determined to be in the range of 1-15 nM for Abeta40 as well as for Abeta42 (FIG. 10).

Example 6

Mass Determination

The exact mass of ESBA212 was determined by electrospray mass spectroscopy. Therefore, ESBA212 was purified and measured in 50% acetonitrile/0.2% formic acid (pH2). Mass spectra (neutral mass) were deconvoluted using the MaxEnt1 software.

Figure 11:
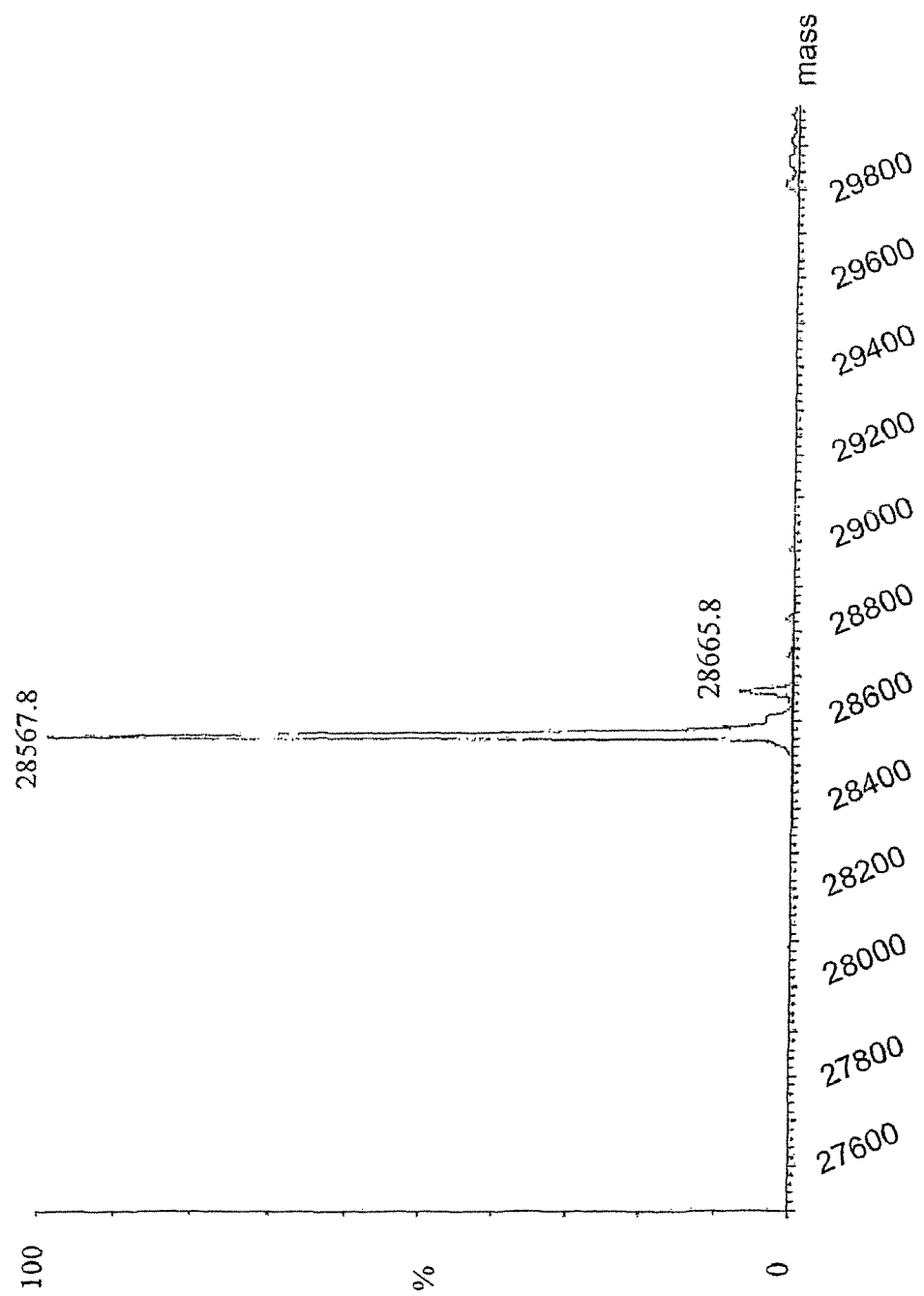
FIG. 11: Mass spectroscopy of ESBA212.

The mass of ESBA212 was determined to be 26517 Da (FIG. 11).

Example 7

Determination of Solubility by PEG-Precipitation

The apparent solubility of ESBA212 was measured in the presence of polyethylene glycol 3000 (PEG3000) according to the method of Atha and Ingham (1981). ESBA212 (20 mg/ml) was incubated with equal volumes of buffer containing different concentrations of PEG3000 (30-50%) resulting in a final protein concentration of 10 mg/ml and a final PEG concentration of 15-25%. After 30 minutes of incubation at room temperature the samples were centrifuged and the protein concentration in the supernatant determined from the absorbance at 280 nm. The apparent solubility was calculated by plotting the PEG concentration against the logarithm of the protein concentration measured in the supernatant. The solubility was determined by extrapolation to 0% PEG.

The solubility of ESBA212 was determined to be about 20 mg/ml.

Example 8

Determination of Thermal Stability

The thermal stability of ESBA212 was determined by measuring the Fourier transform-infrared (FT-IR) spectrum on a Bruker Tensor 27 spectrometer as the temperature is increased from 25-95° C. ESBA212 was left to equilibrate at each temperature for 1-2 minutes before the spectrum was measured.

Figure 12:
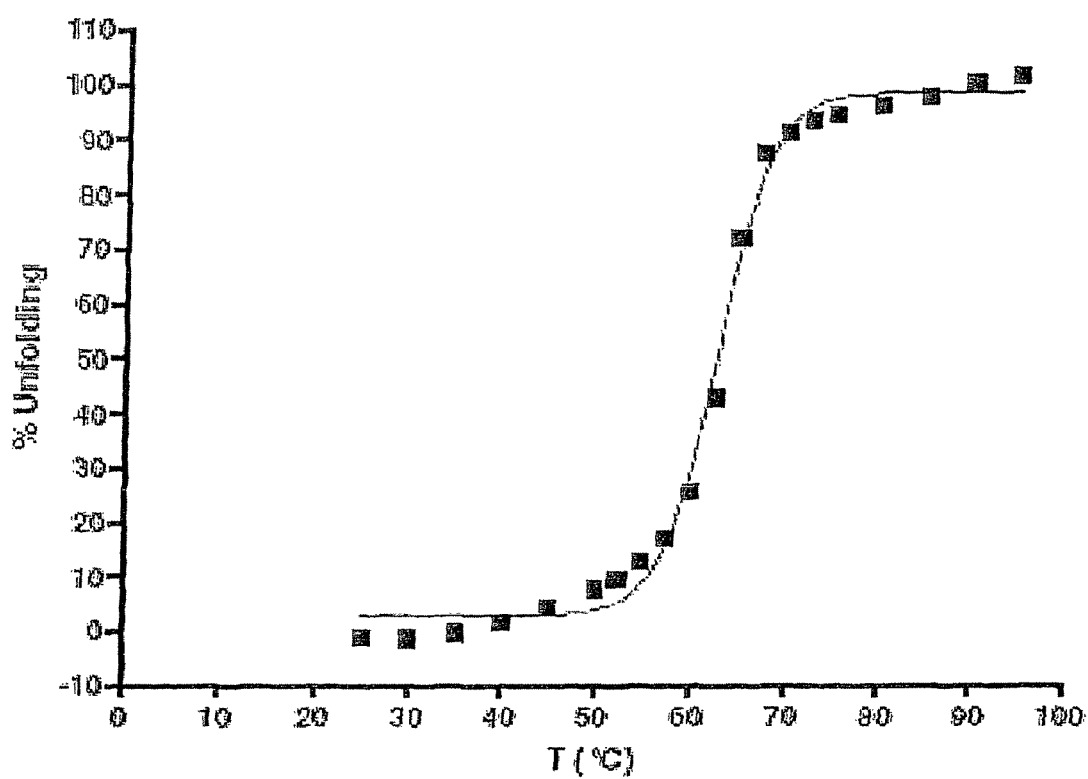
FIG. 12 depicts a FT-IR spectrum, showing the percentage unfolding of ESBA212 at different temperatures, ranging from 25 to 95° C.
Figure 13:
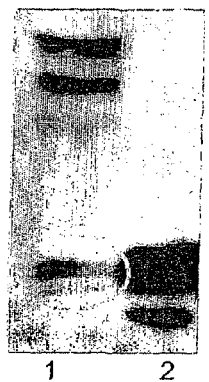
FIG. 13: Western blot showing the stability of ESBA212 incubated in the presence (lane 1) or absence (lane 2) of mouse brain homogenate.

The melting temperature of ESBA212 (50% unfolding of the protein) was determined to be at 62.8° C. However, the unfolding of ESBA212 starts already at about 40° C. (FIG. 12).

Example 9

Prevention of Abeta Aggregation In Vitro

It was investigated whether ESBA212 was able to inhibit the formation of Abeta42 oligomerisation. Therefore, a thioflavine T assay was performed in solution. Thioflavine T associates rapidly with aggregated Abeta fibrils, giving rise to enhanced emission at 482 nm as opposed to the 445 nm of the free dye. This change is dependent on the aggregated state of Abeta as monomeric or dimeric peptides do not react (LeVine III, 1993).

Figure 14:
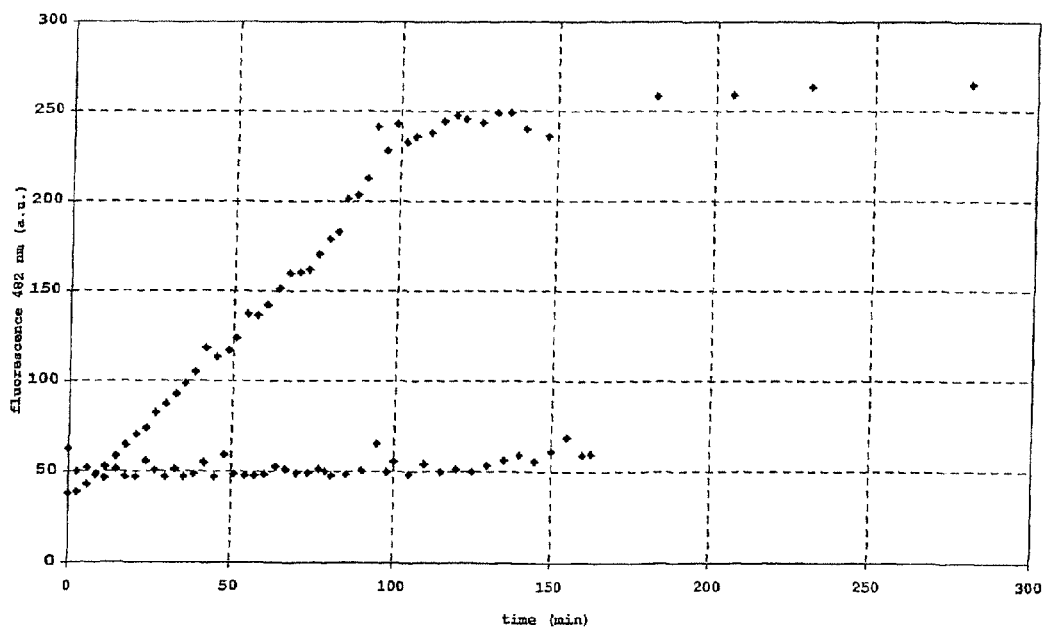
FIG. 14: Result of a thioflavine T assay demonstrating that ESBA212 inhibits Abeta42 oligmerisation in vitro.

2.5 µM Abeta42 were incubated with or without 2.27 µM ESBA212 in the presence of thioflavine T and 500 mM NaCl. As can be seen in FIG. 14 the presence of ESBA212 clearly inhibits the Abeta oligomerisation in vitro over 3 hours as the fluorescence measured at 482 nm does not rise. In contrast, when no ESBA212 was added to the solution higher values of fluorescence were measured indicating the formation of Abeta aggregates.

Example 10

In Vivo Characterization of Pharmacokinetic Properties

In order to determine the pharmacokinetic properties of ESBA212, APP-transgenic mice as well as non-transgenic littermates were treated intravenously or intraperitoneally with a single injection of ESBA212. At predefined time points after the injection blood was drawn retro-orbitally, the amount of ESBA212 in the serum measured by quantitative ELISA and the data analysed using the PK-Summit software.

Animals: For the pharmacokinetic experiments an Alzheimer mouse model was used that was generated by Prof. Dr. R. Nitsch (University of Zurich). These mice (PrP-APP Sw/Arc 10+) over-express the human APP695 containing both the Swedish and the Arctic mutation in a single construct under the control of the prion protein promoter (Knobloch et al, 2006). The mice were bred on the hybrid background of C57BL/6 and DBA/2 preventing the occurrence of health and breeding problems. The characteristics of this strain are: i) the formation of early intracellular Abeta deposits that is associated with impaired cognitive functions from the age of 6 month; ii) the formation of plaques starting at the age of 7 month and highly increasing over the next few month. This development of beta-amyloid plaques coincides with severe cerebral amyloid angiopathy (CAA) (Knobloch et al. 2006).

The mice used for the pharmacokinetic studies were at the age of 6 month.

Experimental procedure: The pharmacokinetic parameters were determined after intravenous or intraperitoneal injection of ESBA212. In case of the intravenous treatment APP-transgenic mice and non-transgenic littermates were used. 7 groups of 2 animals received a single intravenous injection of 15 mg/kg ESBA212 in PBS, pH 6.5. Blood was drawn retro-orbitally at predefined time points (10 and 30 minutes, 1, 2, 4, 8, 12, and 24 h) in a way that 4 samples per time point could be collected (exception: only 2 samples at 10 min and 24 h). ESBA212 concentrations in the serum were measured by a quantitative ELISA.

In case of the intraperitoneal application of ESBA212, only APP-transgenic mice were used. 7 groups of 2 animals received a single intraperitoneal injection of 20 mg/kg ESBA212 in PBS, pH 6.5. Blood samples were collected as described above for the intravenous treatment.

Results: After intravenous injection of ESBA212 the systemic PK followed a bi-phasic clearance. Upon injection there was a clear distribution phase ($\alpha$-elimination, 0-1 h) as well as a terminal elimination phase ($\beta$-elimination, 8-12 h) observed (FIG. 15). There was no significant difference in the $\alpha$-elimination (0.26 versus 0.23 h) and terminal half-life (8.79 versus 7.11 h) in the transgenic and non-transgenic mice, respectively (Table 1). Also the other calculated PK-values were comparable in the transgenic and non-transgenic mice. However, the observed volume of distribution (Vd) is quite high (77.69 and 76.72 ml). This might hint that ESBA212 penetrates very well and quickly into the tissue. In contrast, there were differences observed in the pharmacokinetics when ESBA212 was applied intraperitoneally. A clear absorption phase could be detected with a peak ESBA212 serum concentration at 1 hour after the injection. Then the distribution half-life was about 5 times longer than after intravenous application which might give an indication that a depot effect was obtained when injected via the intraperitoneal route. However, the calculated terminal half-life was slightly shorter after intraperitoneal than intravenous injection. A clear difference was also detected in the mean residence time (MRT) of ESBA212 in the organism, which was about 3 times longer when the scFv was injected intraperitoneally instead of intravenously. The observed differences in the AUC (area under curve), Volume of distribution (Vd) and clearance (CL) between the intravenous and intraperitoneal route of injection could be explained by the fact that the animals treated intraperitoneally received a higher dose of ESBA212 (20 mg/kg instead of 15 mg/kg). When calculating the PK-parameters for an intraperitoneal dose of 15 mg/kg based on the values obtained for 20 mg/kg the following parameters were obtained: no changes in absorption, distribution and elimination half-life as well as in the MRT. However, the AUC (79.124 ug-h/ml), Vd (67.52 ml) and CL (7.84 ml/h) were then comparable to the values obtained after intravenous injection.

TABLE 1

Pharmacokinetic parameters after intravenous and intraperitoneal injection of ESBA212.

| | | PrP-APP Sw/Arc (tg) | PrP-APP Sw/Arc (non-tg) | PrP-APP Sw/Arc (tg) |
|---|---|---|---|---|
| route of application | | i.v. | i.v. | i.p. |
| dosage | mg/kg | 15 | 15 | 20 |
| absorption half-life | h | | | 0.10 |
| distribution half-life | h | 0.26 | 0.23 | 1.28 |
| elimination half-life | h | 8.79 | 7.11 | 5.84 |
| area under curve (AUC) | µg-h/ml | 80.663 | 66.292 | 105.491 |
| mean residence time (MRT) | h | 1.23 | 1.72 | 4.32 |
| volume of distribution (Vd) | ml | 77.69 | 76.72 | 50.62 |
| clearance (CL) | ml/h | 6.06 | 7.38 | 5.88 |

Example 11

In Vivo Plaque Labelling

It was investigated whether ESBA212 was able to bind to amyloid plaques when applied intravenously or intranasally. Therefore, transgenic SwePS1 mice were treated 3 times every 24 h with 210 µg of ESBA212 either by the intravenous or intranasal route of application. 72 h after the first application the animals were perfused with PBS and the brains analysed for the presence of ESBA212. ESBA212 bound to amyloid plaques in the brain both after intravenous and intranasal application of the scFv (FIG. 16). A thioflavine S staining confirmed that ESBA212 really bound to amyloid plaques. Consecutive brain sections of a SwePS1 mouse that was treated intranasally with ESBA212 showed the same staining pattern for ESBA212 and thioflavine S (FIG. 17).

Example 12

PET-Imaging with $^{64}$Cu-Labelled ESBA212

$^{64}$Cu-labelling of ESBA212: ESBA212 was coupled to a CPTA chelator (an approximately 200 Da macrocycle with 4 N-atoms) which binds to the isotope (half-life of 64Cu is 12.7 hours). The chelator was coupled to lysine residues within the ESBA212. As the coupling was mild not every lysine was labelled. It was shown by mass determination that on average two CPTA molecules were bound to each ESBA212 molecule.

Example 13

Ex Vivo Labelling of Plaques by Cu-ESBA212

In order to define whether 64Cu-ESBA212 was still able to bind to amyloid plaques, immunohistochemical stainings on fixed and non-fixed SwePS1 mouse brain sections were performed. The $^{64}$Cu-labelling did not change the binding properties of ESBA212 as $^{64}$Cu-ESBA212 was still able to bind to amyloid plaques on fixed as well as non-fixed brain sections (FIG. 18).

Example 14

In Vivo Labelling of Plaques by Cu-ESBA212

The binding properties of coldly labelled Cu-ESBA212 were investigated in vivo using transgenic SwePS1 mice. The mice received an intranasal application of either 210 ug ESBA212 or 100 ug Cu-ESBA212. The animals were sacrificed 24 or 48 hours after the application and the brains were analysed for the binding of ESBA212 and Cu-ESBA212, respectively, to amyloid plaques.

Figure 19:
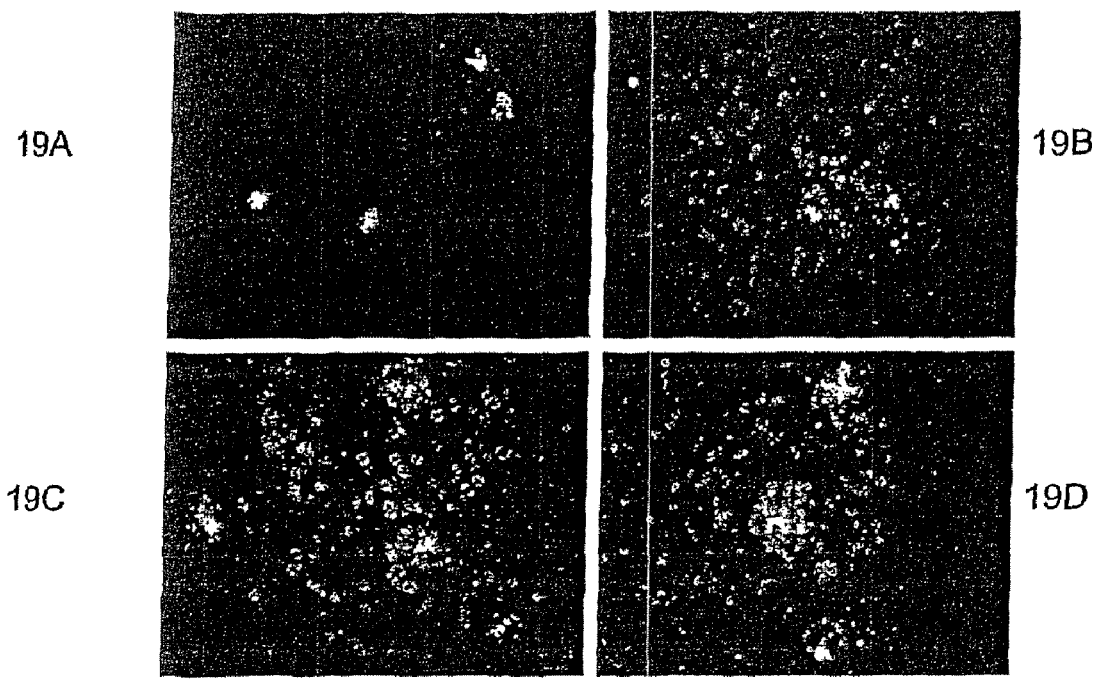
FIG. 19: Detection of bound ESBA212 and Cu-ESBA212 on mouse (SwePS1) brain sections 24 hours and 48 hours after intranasal application.

As seen in FIG. 19, ESBA212 could be detected after 24 as well as 48 hours post application. The same result was observed for the Cu-labelled ESBA212. Therefore, the binding properties of Cu-ESBA212 did not change in vivo compared to ESBA212 as it was already demonstrated for the ex vivo labelling.

Example 15

Elimination Via Kidney

In order to get some information about the elimination pathway of ESBA212 the scFv was injected intravenously into mice. Animals were sacrificed shortly afterwards and the kidneys analysed by immunohistochemical methods.

Figure 20:
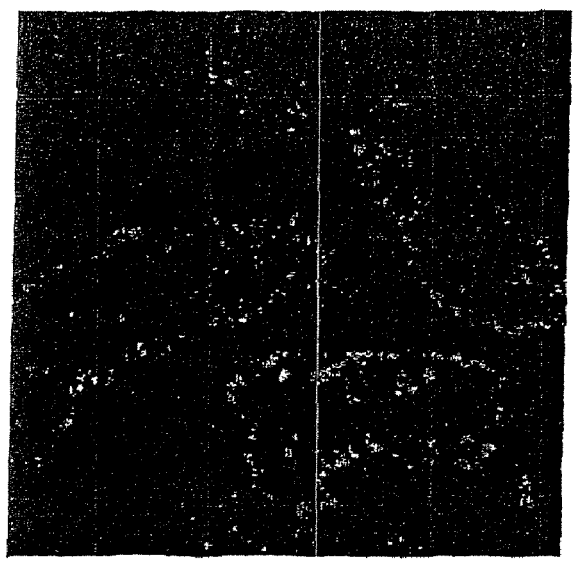
FIG. 20: Detection of ESBA212 in the kidney following an intravenous ESBA212 injection.

ESBA212 is filtered into the primary urine in the kidney and reabsorbed in the proximal tubulus where it is degraded most probably via the lysosomal pathway (FIG. 20).

Example 16

In Vivo Plaque Labelling

A further test similar to the test performed in Example 11 was made with intranasal administration.

Figure 21A:
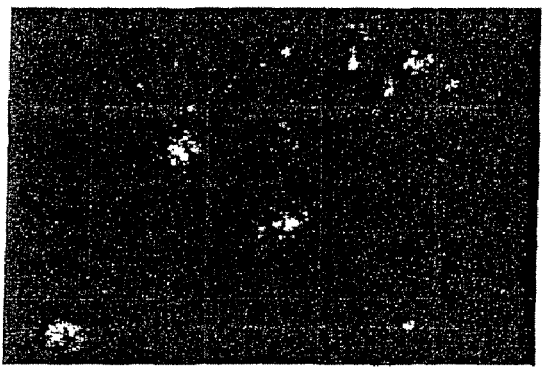
FIG. 21A: Stained with anti-His antibody
Figure 21B:
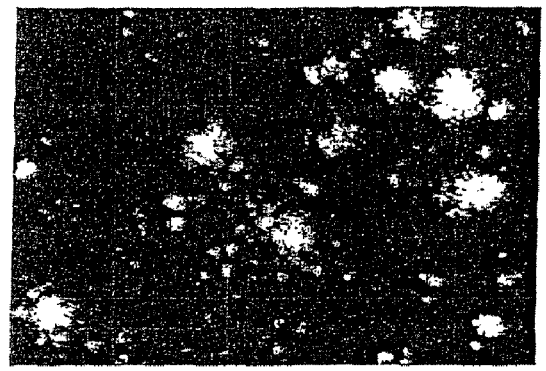
FIG. 21B: Control stained with 6E10
Figure 21C:
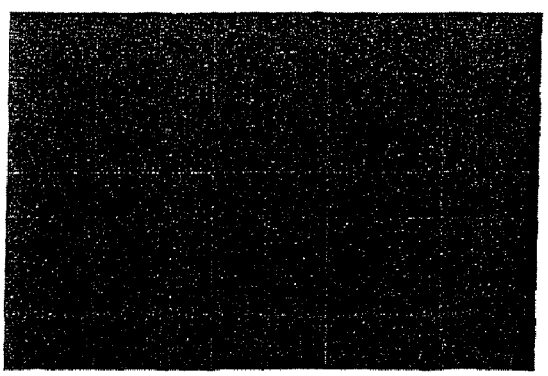
FIG. 21C: Negative control stained with anti-rabbit Cy3
Figure 21D:
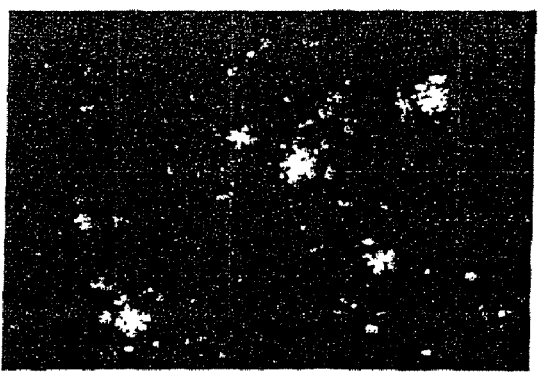
FIG. 21D: Control stained with 22c4 IgG.

Transgenic SwePS1 mice were treated intranasally with 200 µg of ESBA212. The animal was perfused 1 h after intranasal treatment. Aβ-staining on fixed SwePS1 mouse brain slices was performed and recorded as follows:
Stained with anti-His antibody (FIG. 21A)
Control stained with 6E10 (FIG. 21B)
Negative control stained with anti-rabbit Cy3 (FIG. 21C)
Control stained with 22c4 IgG (FIG. 21D)

Example 17

Figure 22A:
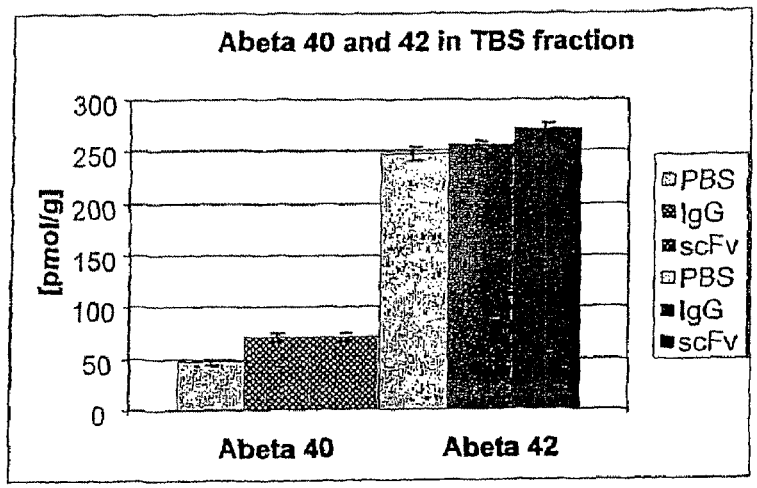
FIG. 22A: soluble fraction (TBS)
Figure 22B:
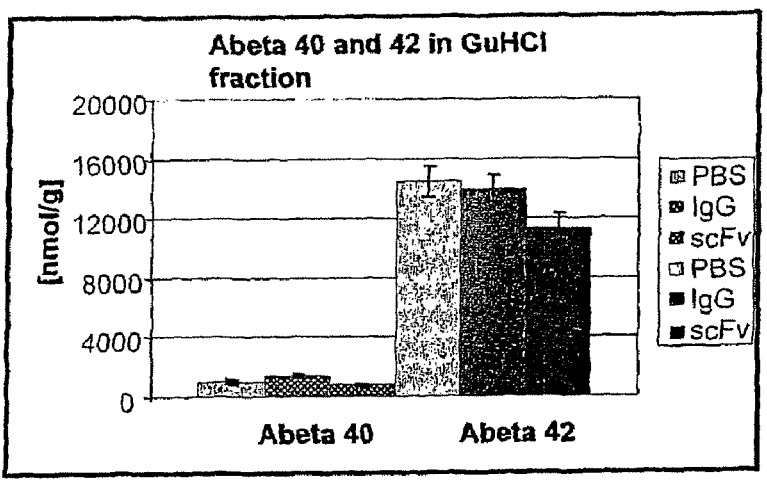
FIG. 22B: insoluble fraction (GuHCl)
Figure 22C:
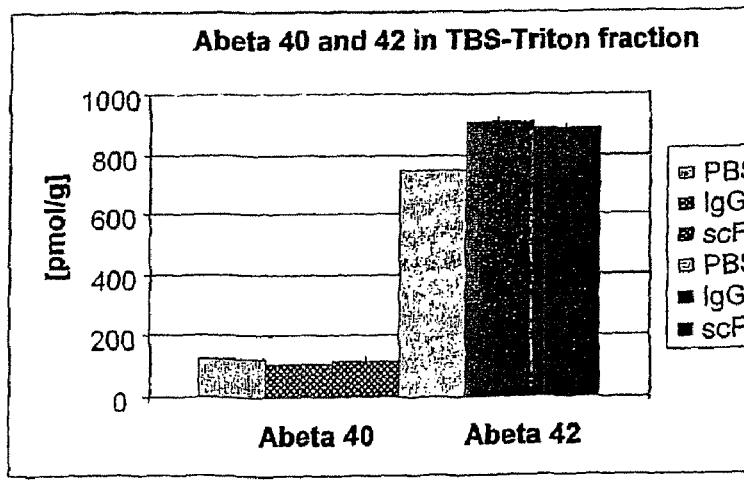
FIG. 22C: membrane-bound fraction (TBS-Triton)

APPswe/PS1ΔE9 mice were treated for 3 months with PBS, 22c4 IgG once a week each and with ESBA212 twice a week. At the end of the treatment the animals were perfused, the brain was isolated and divided into two portions. One portion was homogenized and several extracts were produced and the brain Aβ 40 and 42 levels were determined using a commercial ELISA test (The Genetics Company). It was found that the Aβ 40 and 42 levels were increased in the soluble fraction (TBS) and decreased in the insoluble fraction (GuHCl). In the membrane-bound fraction (TBS-Triton) the Aβ40 level remained unchanged whereas the Aβ 42 level was increased (see FIG. 22). This points to a redistribution of Aβ from the insoluble to the soluble fraction.

The other portion was used for histology. Paraffin sections of treated APPswe/PS1ΔE9 mice were stained with 6E10. Plaque number and area was evaluated using ImageJ software.

Figure 23A:
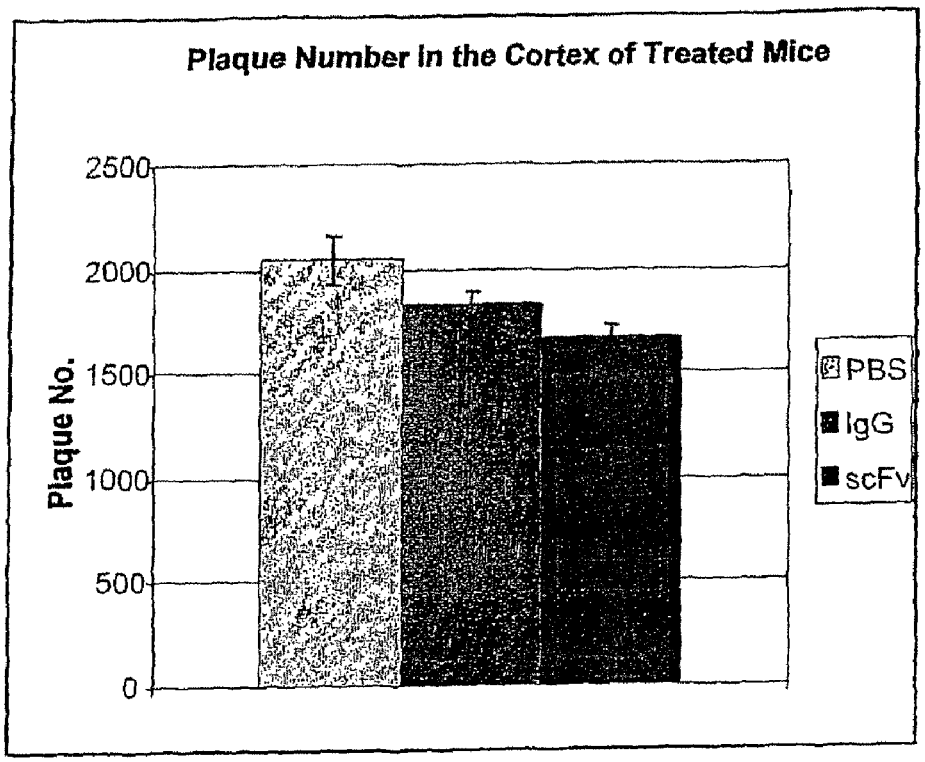
FIG. 23A: Plaque number
Figure 23B:
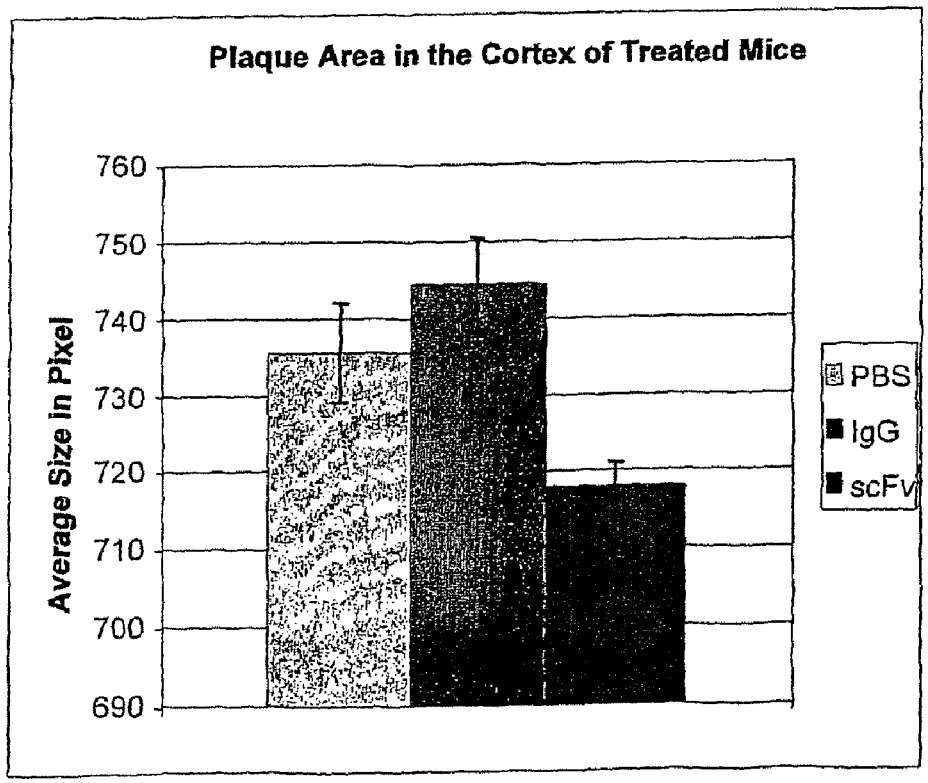
FIG. 23B: Plaque area.

The experiment revealed that animals treated with ESBA212 show a significantly reduced number and also a decreased size of amyloid-plaques (see FIG. 23). This further supports the idea that ESBA212 binds to Aβ fibrils and subsequently breaks them up into monomers or small oligomers, which shifts the equilibrium towards soluble Aβ pools.

The above shown results support the finding that ESBA212 enters the brain after intravenous and intranasal application, and binds to Abeta plaques in the cortex and hippocampus of transgenic mice. Moreover, APPswe/PS1ΔE9 mice treated intranasally with scFv exhibited reduced number and average size of amyloid plaques in the cortex, as well as reduced levels of Aβ42 in the insoluble fraction of brain extracts.

While there are shown and described presently preferred embodiments of the invention, it is to be distinctly understood that the invention is not limited thereto but may be otherwise variously embodied and practised within the scope of the following claims.

REFERENCES

Alfthan et al. (1995) Protein Eng. 8:725-731.
Altschul et al., (1997) Nucleic Acids Res. 25(17):3389-3402.
Altschul, S. F., Gish, W., Miller, W., Myers, E. W. & Lipman, D. J. (1990) "Basic local alignment search tool." J. Mol. Biol. 215:403-410.
Atha, Donald H. and Ingham, Kenneth C. (1981): Mechanism of precipitation of proteins by polyethylene glycols, JBC 256: 12108-12117.
Bacskai, B. J., Kajdasz, S. T., Christie, R. H., Carter, C., Games, D., Seubert, P., Schenk, D. and Hyman, B. T. (2001): Imaging of amyloid-beta deposits in brains of living mice permits direct observation of clearance of plaques with immunotherapy. Nat. Med. 7, 369-372.
Bacskai, B. J., Kajdasz, S. T., McLellan, M. E., Games, D., Seubert, P., Schenk, D. and Hyman, B. T. (2002): Non-Fcmediated mechanisms are involved in clearance of amyloid-beta in vivo by immunotherapy. J. Neurosci. 22, 7873-7878.
Bard, F., Cannon, C., Barbour, R., Burke, R. L., Games, D., Grajeda, H., Guido, T., Hu, K., Huang, J., Johnson-Wood, K., Khan, K., Kholodenko, D., Lee, M., Lieberburg, I., Motter, R., Nguyen, M., Soriano, F., Vasquez, N., Weiss, K., Welch, B., Seubert, P., Schenk, D. and Yednock, T. (2000): Peripherally administered antibodies against amyloid beta-peptide enter the central nervous system and reduce pathology in a mouse model of Alzheimer disease. Nat. Med. 6, 916-919.
Brookmeyer R, Johnson E, Ziegler-Graham K, Arrighi H M (2007): Forecasting the global burden of Alzheimer's disease. Alzheimer's & Dementia: The Journal of the Alzheimer's Association (Vol. 3 (3)).
Burmester, J. and Plückthun, A. (2001): Construction of scFv fragments from hybridoma or spleen cells by PCR assembly, in: Antibody Engineering, R. Kontermann and S. Dübel, Eds., Springer-Verlag, Berlin Heidelberg, pp. 19-40.
Chothia, C., and Lesk, A. M. (1987). Canonical structures for the hypervariable regions of immunoglobulins. J Mol Biol 196, 901-917.
Davies, D. R. et al., "Antibody-Antigen Complexes" Ann. Rev. Biochem. 59:439-473 (1990).
DeMattos, R. B., Bales, K. R., Cummins, D. J., Dodart, J. C., Paul, S. M. and Holtzman, D. M. (2001): Peripheral anti-Abeta antibody alters CNS and plasma Abeta clearance and decreases brain Abeta burden in a mouse model of Alzheimer's disease. Proc. Natl. Acad. Sci. USA 98, 8850-8855.
Frenkel, D., Katz, O. and Solomon, B. (2000): Immunization against Alzheimer's beta-amyloid plaques via EFRH phage administration. Proc. Natl. Acad. Sci. USA 97, 11455-11459.
Gaugler, M., Tracy, J., Kuhnle, K., Crameri, A., Nitsch, R. M. and Mohajeri, M. H. (2005): Modulation of Alzheimer's pathology by cerebro-ventricular grafting of hybridoma cells expressing antibodies against Abeta in vivo. FEBS Letters 579, pp. 753-756.
Güntert, A., Döbeli, H. and Bohrmann, B. (2006): High sensitivity analysis of amyloid-beta peptide composition in anyloid deposits from human and PS2APP mouse brain. Neuroscience 143: 461-475.
Holliger, P. and Hudson, P. (2005), Nat. Biotechnol. 23(9), pp. 1126-1136.
Kabat E A, Wu T T, Perry H M, Gottesman K S, Foeller C. 1991. Sequences of proteins of immunological interest. 5th ed. Bethesda, Md.: National Institutes of Health.
Klein, W. L. (2002): Ab toxicity in Alzheimer's disease: globular oligomers (ADDLs) as new vaccine and drug targets. Neurochemistry International 41: 345-352
Knobloch, M., Konietzko, U., Krebs, D. C., and Nitsch, R. M. (2006): Intracellular Abeta and cognitive deficits precede beta-amyloid deposition in transgenic arcAbeta mice. Neurobiol Aging. 2007 September; 28(9):1297-306. Epub 2006 Jul. 31.
LeVine III, H. (1993): Thioflavine T interaction with synthetic Alzheimer's disease beta-amyloid peptides: Detection of amyloid aggregation in solution. Protein Science 2: 404-410.
Miller, R. et al. (1983): Monoclonal antibody therapeutic trials in seven patients with T-cell lymphoma. Blood 62:988-995.
Mohajeri, M. H., Gaugler, M., Martinez, J., Tracy, J., Li, H., Crameri, A., Kuehnle, K., Wollmer, Am. A. and Nitsch, R. M. (2004): Assessment of the bioactivity of Antibodies against beta-amyloid peptide in vitro and in vivo. Neurodegenerative dis. 1, pp. 160-167.
Schroff, R. et al. (1985): Human anti-murine immunoglobulin responses in patients receiving monoclonal antibody therapy. Cancer Research 45:879-885.
Wörn A, Auf der Maur A, Escher D, Honegger A, Barberis A, Pluckthun A. (2000): Correlation between in vitro stability and in vivo performance of anti-GCN4 intrabodies as cytoplasmic inhibitors. J Biol Chem. 275(4):2795-803.

The invention claimed is:

1. An isolated antibody that selectively binds to the C-terminal part of beta-amyloid, the antibody comprising a variable light chain fragment (VL) sequence comprising the variable light chain CDR1, CDR2 and CDR3 sequences set forth in SEQ ID Nos. 1, 2 and 3, respectively, and a variable heavy chain fragment (VH) sequence comprising the variable heavy chain CDR1, CDR2 and CDR3 sequences set forth in SEQ ID Nos. 4, 5 and 6, respectively, wherein:
   a) position 1 of the light chain is an aspartate residue;
   b) position 43 of the light chain is a proline residue;
   c) position 46 of the light chain is an alanine residue;
   d) position 61 of the light chain is an arginine residue;
   e) position 104 of the light chain is a leucine residue;
   f) position 105 of the light chain is a glutamate residue; and
   g) position 106 of the light chain is a valine residue, according to Kabat numbering.

2. The antibody of claim 1, wherein:
   a) position 9 of the heavy chain is a proline residue;
   b) position 28 of the heavy chain is a threonine residue;
   c) position 71 of the heavy chain is a valine residue;
   d) position 73 of the heavy chain is an arginine residue;
   e) position 75 of the heavy chain is a serine residue;
   f) position 76 of the heavy chain is a serine residue; and
   g) position 78 of the heavy chain is an alanine residue, according to Kabat numbering.

3. The antibody of claim 1, comprising the variable heavy chain fragment (VH) sequence set forth in SEQ ID: No. 17.

4. The antibody of claim 1, comprising the variable light chain fragment (VL) sequence set forth in SEQ ID NO: 7.

5. The antibody of claim 1, further comprising the sequence set forth in SEQ ID NO: 25.

6. The antibody of claim 1, demonstrating the characteristics of:
   (i) binding to both beta-amyloid$_{40}$ and beta-amyloid$_{42}$, with a high and substantially identical affinity;
   (ii) displaying a high affinity for oligomeric and monomeric forms of beta-amyloid; and/or
   (iii) having a solubility of at least 5 mg/ml.

7. The antibody of claim 6, further demonstrating at least one of the following characteristics:
   (iv) mediating the uptake of fibrillar beta-amyloid by microglia;
   (v) binding beta-amyloid plaques; and/or
   (vi) removing beta-amyloid fibrils in the brain and/or inhibiting the formation of amyloid fibrils in the brain.

8. The antibody of claim 1, wherein the antibody inhibits oligomerization of beta-amyloid.

9. The antibody of claim 1, wherein the antibody is a full-length antibody.

10. The antibody of claim 1, being an antigen-binding fragment wherein the antigen-binding fragment is an Fv fragment, a single domain fragment, a single chain antibody (scFv), a Fab fragment or a F(ab')$_2$ fragment.

11. The antibody of claim 1, linked to a therapeutic agent.

12. The antibody of claim 1, being chemically modified.

13. The antibody of claim 1, linked to a label.

14. The antibody of claim 13, wherein the label comprises $^{64}$Cu.

15. A diagnostic or scientific tool comprising the antibody of any one of claim 1, 12 or 13.

16. A test kit comprising the antibody of any one of claim 1, 12 or 13.

17. A diagnostic or scientific tool comprising the antibody of claim 12.

18. A diagnostic or scientific tool comprising the antibody of claim 13.

19. A test kit comprising the antibody of claim 12.

20. A test kit comprising the antibody of claim 13.

21. A pharmaceutical composition for treating or delaying the progression of Alzheimer's disease comprising the antibody of claim 1.

22. An isolated antibody that selectively binds to the C-terminal part of beta-amyloid, wherein the antibody comprises the variable light chain fragment (VL) sequence set forth in SEQ ID NO: 7 and the variable heavy chain fragment (VH) sequence set forth in SEQ ID NO: 17.

23. The antibody of claim 22, wherein the antibody is a full-length antibody.

24. The antibody of claim 22, being an antigen-binding fragment wherein the antigen-binding fragment is an Fv fragment, a single domain fragment, a single chain antibody (scFv), a Fab fragment or a F(ab')$_2$ fragment.

25. An isolated antibody that selectively binds to the C-terminal part of beta-amyloid, wherein the antibody comprises SEQ ID NO: 24.

26. The antibody of claim 22 or 25 being chemically modified.

27. A diagnostic or scientific tool comprising the antibody of claim 26.

28. A test kit comprising the antibody of claim 26.

29. The antibody of claim 22 or 25 linked to a therapeutic agent.

30. The antibody of claim 22 or 25 linked to a label.

31. The antibody of claim 30, wherein the label comprises $^{64}$Cu.

32. A diagnostic or scientific tool comprising the antibody of claim 30.

33. A test kit comprising the antibody of claim 30.

34. The antibody of claim 22 or 25 demonstrating the characteristics of:
   (i) binding to both beta-amyloid$_{40}$ and beta-amyloid$_{42}$, with a high and substantially identical affinity;
   (ii) displaying a high affinity for oligomeric and monomeric forms of beta-amyloid; and/or
   (iii) having a solubility of at least 5 mg/ml.

35. The antibody of claim 34, further demonstrating at least one of the following characteristics:
   (iv) mediating the uptake of fibrillar beta-amyloid by microglia;

(v) binding beta-amyloid plaques; and/or
(vi) removing beta-amyloid fibrils in the brain and/or inhibiting the formation of amyloid fibrils in the brain.

36. A diagnostic or scientific tool comprising the antibody of claim 22 or 25.

37. A test kit comprising the antibody of claim 22 or 25.

38. A pharmaceutical composition for treating or delaying the progression of Alzheimer's Disease comprising the antibody of claim 22 or 25.

39. The antibody of claim 22 or 25, wherein the antibody inhibits oligomerization of beta-amyloid.

* * * * *